United States Patent [19]
Kamb et al.

[11] Patent Number: 6,060,240
[45] Date of Patent: *May 9, 2000

[54] METHODS FOR MEASURING RELATIVE AMOUNTS OF NUCLEIC ACIDS IN A COMPLEX MIXTURE AND RETRIEVAL OF SPECIFIC SEQUENCES THEREFROM

[75] Inventors: Alexander Kamb; Michael John Feldhaus, both of Salt Lake City, Utah

[73] Assignee: Arcaris, Inc., Salt Lake City, Utah

[ * ] Notice: This patent issued on a continued prosecution application filed under 37 CFR 1.53(d), and is subject to the twenty year patent term provisions of 35 U.S.C. 154(a)(2).

[21] Appl. No.: 08/764,191

[22] Filed: Dec. 13, 1996

[51] Int. Cl.[7] .............................. C12Q 1/68; C12P 19/34; C07H 21/04; C12N 15/63
[52] U.S. Cl. ........................ 435/6; 435/91.2; 435/172.3; 435/320.1; 536/23.1; 536/25.4
[58] Field of Search ........................ 435/6, 172.3, 320.1, 435/91.2; 536/25.4, 23.1; 935/77, 78

[56] References Cited

U.S. PATENT DOCUMENTS

| | | |
|---|---|---|
| 4,413,070 | 11/1983 | Renbaum . |
| 4,415,732 | 11/1983 | Caruthers et al. . |
| 4,458,066 | 7/1984 | Caruthers et al. . |
| 4,569,774 | 2/1986 | Webb . |
| 4,678,814 | 7/1987 | Renbaum . |
| 4,725,677 | 2/1988 | Koster et al. . |
| 4,973,679 | 11/1990 | Caruthers et al. . |
| 4,980,460 | 12/1990 | Molko et al. . |
| 5,149,625 | 9/1992 | Church et al. ............... 435/6 |
| 5,604,097 | 2/1997 | Brenner ....................... 435/6 |

FOREIGN PATENT DOCUMENTS

| | | |
|---|---|---|
| 0 395398 | 10/1990 | European Pat. Off. . |
| WO 91/14768 | 10/1991 | WIPO ................ G12N 5/08 |
| WO 92/04384 | 3/1992 | WIPO . |
| WO 93/02214 | 2/1993 | WIPO ................ C12Q 1/68 |
| WO 93/18068 | 9/1993 | WIPO ................ C07K 17/06 |
| WO 93/21203 | 10/1993 | WIPO . |
| WO 95/08647 | 3/1995 | WIPO ................ C12Q 1/68 |
| WO 95/27080 | 10/1995 | WIPO . |
| WO 95/35505 | 12/1995 | WIPO ................ G01N 33/543 |
| WO 96/12014 | 4/1996 | WIPO . |
| WO 96/12039 | 4/1996 | WIPO . |

OTHER PUBLICATIONS

Pantanjali S.R. et al., "Construction of a Uniform–Abundance (Normalized) cDNA Library"; *Proc. Natl. Acad. Sci. USA;* 88:1943–1947; 1991.
Brenner et al, "Encoded combinatorial chemistry", Proc. Natl. Acad. Sci. 89:5381–5383, Jun. 1992.
Schena et al., Science 270:467–470, Oct. 20, 1995.
Li et al, "Isolation of ORC6, a component of the yeast origin recognition complex by a one–hybrid system", Science 262:1870–1874, Dec. 1993.

(List continued on next page.)

*Primary Examiner*—Jeffrey Fredman
*Attorney, Agent, or Firm*—Fish & Neave; James F. Haley, Jr.; Barbara A. Ruskin

[57] ABSTRACT

The present invention relates to a method for the comparative assessment of the level of specific nucleic acid sequences in samples derived from different sources. More specifically, the invention relates to a method using oligonucleotides covalently linked to a solid support, such as beads, to isolate specific labeled nucleic acid sequences from complex mixtures. The methods disclosed allow quantitative comparisons of the amount of nucleic acid of defined sequence in a plurality of different samples of nucleic acid, e.g., from different cells or tissues or from genetic libraries. Nucleic acids from the samples are labeled in such a fashion that the signals can be distinguished and compared following hybridization to the oligonucleotides on the beads. According to the invention, the solid supports with the hybridized nucleic acid may be retrieved, and the target nucleic acid eluted and analyzed. Furthermore, the invention provides a method for tagging individual clones from a cDNA library such that they can be identified uniquely and retrieved by hybridization to specific beads.

36 Claims, 15 Drawing Sheets

OTHER PUBLICATIONS

Albretsen et al., 1990, "Applications of Magnetic Beads with Covalently Attached Oligonucleotides in Hybridization: Isolation and Detection of Specific Measles Virus mRNA from a Crude Cell Lysate", *Anal. Biochem.* 189:40–50.

Baum, 1996, "Combinatorial Chemistry", *Chemical & Engineering News* Feb. 12 Issue:28–64.

Beattie et al., 1993, "Genosensor Technology", *Clinical Chemistry* 39:719–722.

Beaucage and Iyer, 1992, "Advances in the Synthesis of Oligonucleotides by the Phosphoramidite Approach", *Tetrahedron* 48:2223–2311.

Boerwinkle et al., 1989, "Rapid Typing of Tandemly Repeated Hypervariable Loci by the Polymerase Chain Reaction: Application to the Apolipoprotein B 3' Hypervariable Region", *Proc. Natl. Acad. Sci. U.S.A.* 86:212–216.

Botstein et al., 1980, "Construction of a Genetic Linkage Map in Man Using Restricion Fragment Length Polymorphisms", *Am. J. Hum. Genet.* 32:314–331.

Brown et al., 1989, "A New Base–stable Linker for Solid–phase Oligonucleotide Synthesis", *J. Chem. Soc. Commun.* :891–893.

Bush et al., 1992, "Solid–phase Time–resolved Fluorescence Detection of Human Immunodeficiency Virus Polymerase Chain Reaction Amplification Products", *Anal. Biochem.* 202:146–151.

Damha et al., 1990, "An Improved Procedure for Derivatization of Controlled–pore Glass Beads for Solid–phase Oligonucleotide Synthesis", *Nucleic Acids Research* 18:3813–3821.

Day et al., 1991, "Immobilization of Polynucleotides on Magnetic Particles", *Biochem J.* 278:735–740.

Der et al., 1982, "Transforming Genes of Human Bladder and Lung Carcinoma Cell Lines are Homologous to the ras Genes in Harvey and Kirsten Sarcoma Viruses", *Proc. Natl. Acad. Sci. U.S.A.* 79:3637–3640.

Diatchenko et al., 1996, "Suppression Subtractive Hybridization: A Method for Generating Differentially Regulated or Tissue–specific cDNA Probes and Libraries", *Proc. Natl. Acad. Sci. U.S.A.* 93:6025–6030.

El–Deiry et al., 1993, "WAF1, A Potential Mediator of p53 Tumor Suppression", *Cell* 75:817–825.

Ghosh and Musso, 1987, "Covalent Attachment of Oligonucleotides to Solid Supports", *Nucleic Acids Research* 15:5353–5372.

Grothues et al., 1993, "PCR Amplification of Megabase DNA with Tagged Random Primers (T–PCR)", *Nucleic Acids Research* 21:1321–1322.

Hattier et al., 1995, *Mammalian Genome* 6:873–879.

Hedrick et al., 1984, "Isolation of cDNA Clones Encoding T Cell–specific Membrane–associated Proteins", *Nature* 308:149–153.

Kallioniemi et al., 1992, "Comparative Genomic Hybridization for Molecular Cytogenetic Analysis of Solid Tumors", *Science* 258:818–821.

Kamb et al., 1987, "Molecular Characterization of Shaker, a Drosophila Gene that Encodes a Potassium Channel", *Cell* 50:405–410.

Lam et al., 1991, "A New Type of Synthetic Peptide Library for Identifying Ligand–binding Activity", *Nature* 354:82–84.

Lennon et al., 1996, "The I.M.A.G.E. Consortium: An Integrated Molecular Analysis of Genomes and Their Expression", *Genomics* 33:151–152.

Liang et al., 1995, "Analysis of Altered Gene Expression by Differential Display", *Methods Enzymol* 254:304–321.

Lipshutz et al., 1995, "Using Oligonucleotide Probe Arrays to Access Genetic Diversity", *Biotechniques* 19:442–447.

Lisitsyn and Wigler, 1995, "Representational Difference Analysis in Detection of Genetic Lesions in Cancer", *Methods Enzymol* 254:291–304.

Lund et al., 1988, "Assessment of Methods for Covalent Binding of Nucleic Acids to Magnetic Beads, Dynabeads™, and the Characteristics of the Bound Nucleic Acids in Hybridization Reactions", *Nucleic Acids Research* 16:10861–10880.

Maskos and Southern, 1992, "Oligonucleotide Hybridisations on Glass Supports: A Novel Linker for Oligonucleotide Synthesis and Hybridisation Properies of Oligonucleotides Synthesized in situ", *Nucleic Acids Research* 20:1679–1684.

Meszaros and Morton, 1996, "Subtractive Hybridization Strategy Using Paramagnetic Oligo(dT) Beads and PCR", *BioTechniques* 20:413–419.

*Meth. Enzymol.*, Section A, pp. 11–147, vol. 44 (Academic Press. New York, 1976).

Needels et al., 1993 "Generation and Screening of an Oligonucleotide–encoded Synthetic Peptide Library", *Proc. Natl. Acad. Sci. U.S.A.* 90:10700–10704.

Noda et al., 1994, "Cloning of Senescent Cell–derived Inhibitors of DNA Synthesis Using an Expression Screen", *Exp. Cell. Res.* 211:90–98.

Palazzolo et al., 1989, "Use of a New Strategy to Isolate and Characterize 436 Drosophila cDNA Clones Corresponding to RNAs Detected in Adult Heads but Not in Early Embryos", *Neuron* 3:527–539.

Parada et al., 1982, "Human EJ Bladder Carcinoma Oncogene is Homologue of Harvey Sarcoma Virus ras Gene", *Nature* 297:474–478.

Pon et al., 1988, "Derivatization of Controlled Pore Glass Beads for Solid Phase Oligonucleotide Synthesis", *Biotechniques* 6:768–775.

Puzyrev et al., 1995, "Normalized cDNA Library from Human Erythroleukemia Cells", *Mol Biol* 29:97–103.

Rowley, J.D., 1990, "Molecular Cytogenetics: Rosetta Stone for Understanding Cancer–Twenty–ninth G.H.A. Clowes Memorial Aware Lecture", *Cancer Res.* 50:3816–3825.

Schena et al., 1995, "Quantitative Monitoring of Gene Expression Patterns with a Complementary DNA Microarray", *Science* 270:467–470.

Schutte et al., 1995, "An Integrated High–resolution Physical Map of the DPC/BRCA2 Region at Chromosome 13q12[1]", *Cancer Res.* 55:4570–4574.

Soares et al., 1994, "Construction and Characterization of a Normalized cDNA Library", *Proc. Natl. Acad. Sci. U.S.A.* 91:9228–9232.

Tavtigian et al., 1994, "Cloning of Mid–$G_1$ Serum Response Genes and Identification of a Subset Regulated by Conditional myc Expression", *Mol Biol Cell* 5:375–388.

Telenius et al., 1992, "Degenerate Oligonucleotide–primed PCR: General Amplification of Target DNA by a Single Degenerate Primer", *Genomics* 13:718–725.

van Dekken, et al., 1990, "Targeted Cytogenetic Analysis of Gastric Tumors by in situ Hybridization with a Set of Chromosome–specific DNA Probes", *Cancer* 66:491–497.

Velculescu et al., 1995, "Serial Analysis of Gene Expression", *Science* 270:484–487.

Weber, J.L., 1990, "Human DNA Polymorphisms and Method of Analysis", *Curr. Opin Biotechnol* 1:166–171.

Welsh and McClelland, 1991, "Genomic Fingerprinting using Arbitrarily Primed PCR and a Matrix of Pairwise Combinations of Primers", *Nucleic Acids Research* 19:5275–5279.

Wetmur, J.G., 1991, "DNA Probes: Applications of the Principles of Nucleic Acid Hybridization", *Critical Reviews in Biochemistry and Molecular Biology* 26:227–259.

Wolf et al., 1987, "Rapid Hybridization Kinetics of DNA Attached to Submicron Latex Particles", *Nucleic Acids Research* 15:2911–2926.

Yanagi et al., 1984, "A Human T Cell–Specific cDNA Clone Encodes a Protein Having Extensive Homology to Immunoglobulin Chains", *Nature* 308:145–149.

Zuckermann et al, 1992, "Design, Construction and Application of a Fully Automated Equimolar Peptide Mixture Synthesizer", *Int. J. Pept. Protein Res.* 40:498–507.

Sequence Identifier Tags
1. 8 synthetic coupling reactions
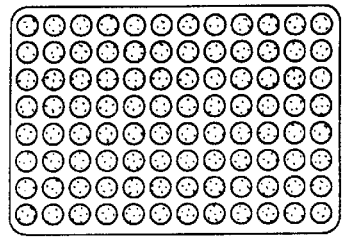
2. Pool and Split
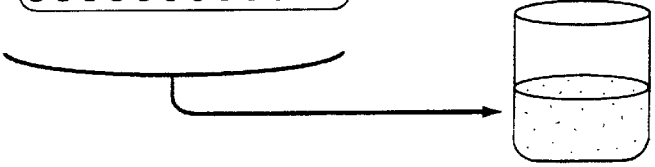
3. 8 further coupling reactions
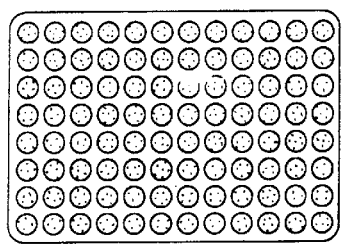
4. Pool and Split
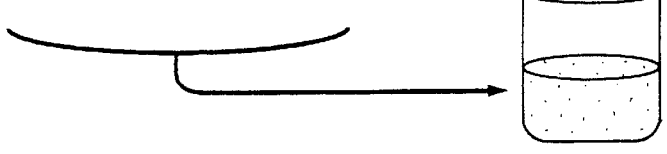
5. 8 further coupling reactions
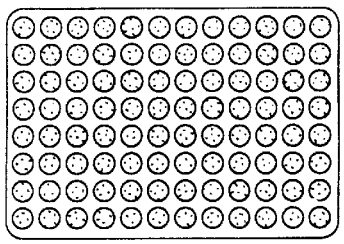
6. Final product: one million 24-mers
FIG. 7

Perfect match
predicted Tm: 72 deg.
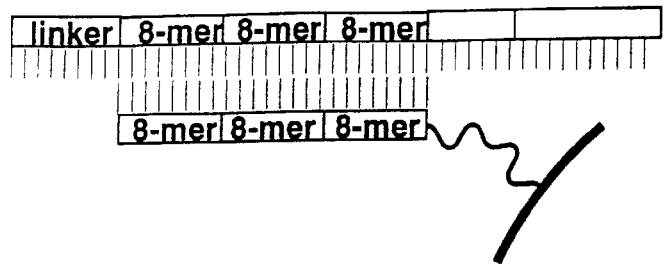
Mismatches
predicted Tm: <48 deg.
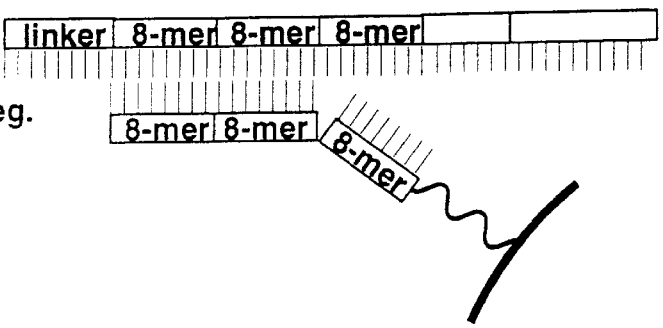
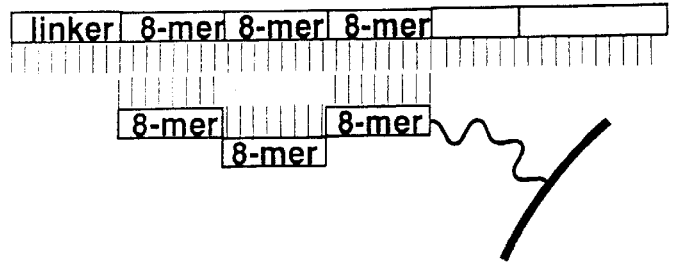
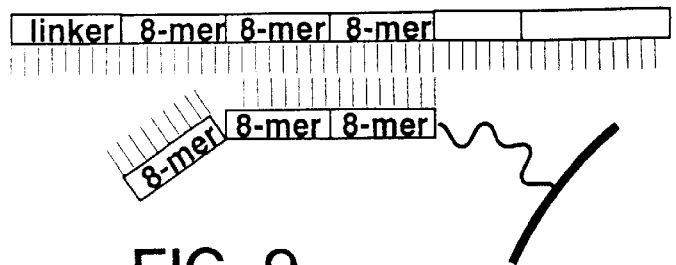
FIG. 9

METHODS FOR MEASURING RELATIVE AMOUNTS OF NUCLEIC ACIDS IN A COMPLEX MIXTURE AND RETRIEVAL OF SPECIFIC SEQUENCES THEREFROM

FIELD OF THE INVENTION

The present invention relates generally to methods for the quantitation and isolation of specific nucleic acids from complex mixtures of nucleic acids. The methods of the invention allow for the comparative assessment of the expression levels of genes in samples derived from different sources, e.g., different tissue or cell types, disease- or development stages.

BACKGROUND OF THE INVENTION

Differential Gene Expression.

The pathology of many diseases involves differences in gene expression; indeed, normal tissue and diseased tissue can often be distinguished by the types of active genes and their expression levels. For example, cancer cells evolve from normal cells to highly invasive, metastatic malignancies, which frequently are induced by activation of oncogenes, or inactivation of tumor suppressor genes. See, The National Cancer Institute, "The Nation's Investment In Cancer Research: A Budget Proposal For Fiscal Years 1997/98", Prepared by the Director, National Cancer Institute, pp. 55–77. Altered expression patterns of oncogenes and tumor suppressor genes in turn effect dramatic changes in the expression profiles of numerous other genes. Differentially expressed sequences can serve as markers of the transformed state and are, therefore, of potential value in the diagnosis and classification of tumors. Differences in gene expression, which are not the cause but rather the effect of transformation, may be used as markers for the tumor stage. Thus, the assessment of the expression profiles of known tumor-associated genes has the potential to provide meaningful information with respect to tumor type and stage, treatment methods, and prognosis. Furthermore, new tumor-associated genes may be identified by systemically comparing the expression of genes in tumor specimens with their expression in control tissue. Genes whose levels are increased in tumors relative to normal cells are candidates for genes encoding growth-promoting products, e.g., oncogenes. In contrast, genes whose expression is reduced in tumors are candidates for genes encoding growth inhibiting products, e.g., tumor suppressor genes or genes encoding apoptosis-inducing products. Generally, the underlying premise is that the profiles of gene expression may point to the physiological function or malfunction of the gene product in the organism.

Pathological gene expression differences are not confined to cancer. Autoimmune disorders, restenosis, atherosclerosis, neurodegenerative diseases, and numerous others can be expected to involve aberrant expression of particular genes. Significant resources have been expended in recent years to identify and isolate genes relevant to these diseases. Accordingly, an efficient method allowing the comparative assessment of the relative amounts of nucleic acids in complex mixtures, and the retrieval of specific nucleic acids from those complex mixtures, would be an extremely valuable tool for genetic and medical research.

In the past, the comparison of the expression levels of specific transcripts among different cell or tissue types, tissues or cells derived from different disease or developmental stages, or from cells exposed to different stimuli has provided meaningful information with respect to a gene's function or its role in the development of a disease. Approaches based on the determination of differences in the expression profiles of genes have facilitated the identification of novel genes encoding products having a function of interest. For example, such approaches have permitted the identification of several genes, for example T cell receptor genes (Yanagi et al., 1984, Nature 308:145–149), and a number of tumor suppressor genes, including p21 (el-Deiry et al., 1993, Cell 75:817–825; Noda et al., 1994, Exp. Cell. Res. 211:90–98). Further, comparative assessment of relative amounts of nucleic acids has the potential to provide a valuable parameter for the organization of sequence information obtained through large scale sequencing approaches. Genetics.

Methods that permit the rapid enrichment and subsequent identification of sequences that cause specific changes in cell behavior are highly desirable. With these methods, specific functions may be assigned to genes or gene fragments based on their activity in cells. Traditional genetics involves isolation of mutants that have particular phenotypes. In combination with modern molecular methods, it is possible to isolate the mutant genes responsible for a specific phenotype. See, e.g., Kamb et al., 1987, Cell 50:405–410. In general, however, the process of positional gene cloning, i.e., cloning a gene based on its genetic location, is laborious. It is also possible to clone genes by expression. For example, several oncogenes have been identified based on their ability to cause cell proliferation when introduced into cells. Der et al., 1982, Proc. Natl. Acad. Sci. U.S.A. 79:3637–3640; Prada et al., 1982 Nature 297:474–478. It is especially valuable to use methods that can not only identify sequences that enhance cell proliferation, but also identify sequences that inhibit cell growth. Even more valuable, are methods that can identify such sequences that have effects specific to certain cell types (e.g., a sequence that inhibits growth of tumor cells but not normal cells). The method described herein is capable of achieving such results.

Differences In Genomic DNA.

Differences in genomic DNA are the underlying basis for differences between species and for much of the individual variation within a species. Furthermore, many pathological disorders, i.e., genetic disorders, are driven by chromosomal mutations. Rowley, 1990, Cancer Res. 50:3816–3825. Identification of differences in the genome and understanding of their effect on the phenotype of the organism provides valuable insight into the development of inherited diseases.

Many methods have been used to characterize variation between different DNA samples. These involve crude methods of analysis such as overall DNA base composition, melting curves, solution hybridization at different stringencies, and measurements of percentages of modified bases and genome size. Progressively more refined methods have been applied over the years including restriction mapping and DNA sequence analysis. Botstein et al., 1980, Am. J. Hum. Genet. 32:314–331; Lipshutz et al., 1995, Biotechniques 19:442–447. Ultimately, the DNA sequence gives the most detailed and reliable information. However, sequencing, as a systematic approach for genomic analysis, is slow and expensive. Indeed, genomic sequencing has been limited to a few particularly interesting genes or genetic intervals.

Thus, there is an unmet need for an efficient method that allows direct screening of genomic DNA to detect differences in DNA sequence, ploidy (copy number), and/or promoter activity in a high through-put manner.

Current Means For The Quantitative Determination Of Relative Amounts Of Specific Nucleic Acids.

The technical hurdles associated with the quantitative determination of relative amounts of nucleic acids, e.g., the determination of MRNA profiles or the determination of sequence ploidy, are daunting. Often, only a few copies of a particular nucleic acid may be present within complex mixtures. For example, many transcripts are present only at a very low abundance. Thus, a highly sensitive method is required to detect as little as one mRNA molecule per cell. In the case of genomic DNA, it might be desired to detect deletions or amplifications against a background of $3 \times 10^9$ base pairs in the human genome. Furthermore, the availability of sample mRNA/cDNA/genomic DNA may be rather limited. Thus, the absolute number of nucleic acid molecules in a sample may be very small. Moreover, the expression levels of genes vary greatly, ranging from a single MRNA molecule per cell up to about 5,000 MRNA molecules per cell. Given 10,000 different MRNA types per cell on average, and a total of 500,000 mRNA molecules per cell, the required detection range is tremendous. Additionally, the level of each specific nucleic acid molecule (MRNA, cDNA, genomic DNA fragment) must be determined separately with a corresponding specific probe, which may be labor- and resource-intensive.

To date, a number of general methods have been developed to quantify nucleic acid molecules. Many of the available methods are suited to assess presence or absence, or relative amounts of specific nucleic acids, in particular mRNA, expressed in different cell or tissue types. However, each of these methods has problems, especially when it is an objective to analyze large numbers of targets and the available amounts of sample nucleic acids are a limiting factor.

A traditional method for the assessment of MRNA expression profiles is Northern blot analysis. Crude RNA or MRNA derived from different sources is separated by gel electrophoresis, and transferred to a nitrocellulose or nylon filter. Immobilized on the filter, the mRNA is hybridized with a probe corresponding to sequences of the gene of interest. See, Sambrook et al., 1990, *Molecular Cloning: A Laboratory Manual.* Cold Spring Harbour Laboratory Press, New York. Northern blot analysis is a highly sensitive approach for determining the expression profile of small numbers of sequences of interest. However, this type of assay is not suited for analysis of large numbers of probes.

A second approach for the determination of MRNA expression profiles based on identification of differentially expressed sequences employs DNA probe hybridization to filters. Palazzolo et al., 1989, *Neuron* 3:527–539; Tavtigian et al., 1994, *Mol Biol Cell* 5:375–388. In this method, phage or plasmid DNA libraries, typically cDNA libraries, are plated at high density on duplicate filters. The two filter sets are screened independently with cDNA prepared from two sources. The signal intensities of the various individual clones are compared between the two duplicate filter sets to determine which clones hybridize preferentially to cDNA from one source compared to the other. These clones are isolated and tested to verify that they represent sequences that are preferentially present in one of the two original samples. The major drawback with this approach is its lack of sensitivity. It is typically impossible to identify differentially expressed sequences that are present in amounts of less than one (1) occurrence in as much as 1,000 to 10,000 sequences. In addition, for detection there must be a relative large disparity in expression of a particular sequence.

A third approach involves the screening of cDNA libraries derived from subtracted mRNA populations. Hedrick et al., 1984, *Nature* 308:149–153. The method is closely related to the method of differential hybridization described above, but the cDNA library is prepared so as to favor clones from one mRNA sample over another. This is typically accomplished by a subtractive step prior to cloning in which the first strand of the cDNA from the first sample is hybridized to an excess of MRNA from the second sample, whereby the DNA/RNA heteroduplexes are removed. The remaining single stranded cDNA is converted into double-stranded cDNA and cloned into a phage or plasmid vector. The subtracted library so generated is depleted for sequences that are shared between the two sources of MRNA, and enriched for those that are uniquely present in the first sample. Clones from the subtracted library can be characterized directly. Alternatively, they can be screened by a subtracted cDNA probe, or on duplicate filters using two different probes as above. The advantage of this method is that the number of clones which need to be screened and analyzed is small. However, differential hybridization is technically very difficult. Furthermore, it lacks sensitivity, and is only suited for identification of differentially expressed sequences that are present in relative amounts higher than about one in $1 \times 10^4$.

A fourth approach involves Expressed Sequence Tag (EST) sequencing. Lennon et al., 1996, *Genomics* 33:151–152. This method involves the direct analysis of individual clones from cDNA libraries by DNA sequencing. Libraries are generated from two sources that are the objects of comparison, and individual inserts of the libraries are sequenced. The frequency of particular sequences reflecting the relative abundance of specific sequences is recorded for each library. The most significant drawback of EST sequencing is its extreme time and resource inefficiency. In order to provide a reasonable sampling of each library, many thousands of individual insert sequences must be analyzed.

A fifth approach is Serial Analysis of Gene Expression (SAGE). Velculescu et al., 1995, *Science* 270:484–487. SAGE is closely related to the above method of EST sequencing. However, the libraries are constructed in such a way that small portions of many individual cDNAs are ligated together in tandem in a single vector. This has, compared to the EST approach, the advantage that multiple cDNAs are analyzed with each sequencing run which greatly reduces the amount of sequencing that must be carried out to achieve a similar level of completeness. Since a stretch of roughly a dozen nucleotides is sufficient in general to determine the identity of a particular transcript, this method is much faster. Each sequencing run can sample up to about fifty transcripts, rather than a single transcript as in the EST sequencing method. Nevertheless, the process is largely serial and necessitates sampling of all cDNAs that are present in equal amounts between the two samples, as well as those that are differentially expressed. This produces significant redundancy.

A sixth approach involves the differential display of MRNA. Liang et al., 1995, *Methods Enzymol* 254:304–321. PCR primers of arbitrary sequence, or designed to optimize the desired pseudo-random amplification, are used to amplify sequences from two mRNA samples by reverse transcription, followed by PCR. The products of these amplification reactions are run side by side, i.e., pairs of lanes contain the same primers but different MRNA samples, on DNA sequencing gels. Differences in the extent of amplification can be detected by eye. Bands that appear to be differentially amplified between the two samples can be excised from the gel and reamplified for characterization. If the collection of primers is suitably large, it is generally possible to identify at least one fragment that is differentially amplified in one sample compared with the second. The disadvantage of the method is its explicit reliance on random events, and the vagaries of PCR, which strongly bias the subset of sequences that can be detected by the method.

Yet another approach is Representational Difference Analysis (RDA) of nucleic acid populations from different samples. Lisitsyn et al., 1995, *Methods Enzymol* 254:291–304. RDA uses PCR to amplify fragments that are not shared between two samples. A hybridization step is followed by restriction digests to remove fragments that are shared from participation as templates in amplification. An amplification step allows retrieval of fragments that are present in higher amounts in one sample compared to the other. Again, the method is subject to the limitations of PCR and DNA hybridization which tend to bias the results strongly toward certain fragments and away from others. Furthermore, the final products of RDA are not representative of the differences that exist between the two input samples. RDA can be used with cDNA or with genomic DNA fragments to identify differences.

An eighth approach for the identification of differentially expressed sequences involves hybridization of labeled MRNA or cDNA in solution to DNA fragments or oligonucleotides attached to a solid support in high density arrays. Schena et al., 1995, *Science* 270:467–470. Since the arrays contain known sequences placed in defined locations, the hybridization signal intensities permit an assignment of the relative amount of target nucleic acid capable of hybridizing to a particular probe sequence. The method is parallel, rapid, and sensitive. Disadvantages are that the sequences in the array must be known beforehand, and that the hybridizing sequences cannot easily be recovered from the surface of the array.

While some of the above methods permit the determination of expression profiles of genes and the identification of sequences that have particular expression patterns, most are not sufficiently efficient and sensitive for comparative assessment of nucleic acids on a large scale. All existing methods have defects in either sensitivity, speed, comprehensiveness, or the ability to recover specific sequences, e.g., from a genetic library.

Therefore, the methods of the present invention, allowing the simultaneous assessment of relative amounts of a multiple MRNA species in two or more samples in an efficient manner and the recovery of sequences that have particular effects on cell phenotypes provide a long desired improvement over currently available methods. The methods of the invention also provide other advantages, such as increasing the throughput of probes, boosting the generation of valuable data, and significantly lowering the time and cost of analysis. Solid supports, specifically beads and microspheres, have been used to bind nucleic acid in solution, but not for the applications described for the invention herein (e.g., Bush et al., 1992, *Anal. Biochem.* 202:146–151; Meszaros and Morton, 1996, *BioTechniques* 20:413–419).

SUMMARY OF THE INVENTION

The present invention relates to a method for the assessment of relative amounts of nucleic acids within a complex mixture of nucleic acids and their retrieval for subsequent analysis. More specifically, the methods of the present invention allow direct assessment of the relative abundance of specific nucleic acids in samples derived from different sources, for example different tissue or cell types, and disease- or developmental stages.

Generally, the invention employs solid supports referred to as beads, that have stably attached to their surface oligonucleotides or nucleic acid fragments, collectively referred to as "capture oligonucleotides". The capture oligonucleotides are synthesized in such a way that each bead contains multiple copies of one oligonucleotide sequence, typically $1 \times 10^6$ to $1 \times 10^{10}$, linked to the bead surface. Thus, the population of beads may contain several million different capture oligonucleotides, each bead having only one type of capture oligonucleotide attached to its surface. The beads with the attached unique capture oligonucleotides are used as hybridization probes in solution. The target nucleic acids are labeled with a marker, preferably a visual marker, most preferably a fluorophore, to permit detection by instruments such as the automated fluorescence activated cell sorter (FACS). Typically, target nucleic acids derived from different sources are labeled with different fluorophores which can readily be distinguished.

In one aspect of the invention, the target nucleic acids from the first source are linked to a first label, and the target nucleic acids from the second source are linked to a second label. The labeled target nucleic acids from the different sources are pooled and contacted with a number of beads each having attached thereto capture oligonucleotides of a unique sequence, under conditions that promote the formation of perfectly matched duplexes between the capture oligonucleotides and nucleic acid molecule complements within the pool. Subsequently, the beads are sorted according to the relative amount of the first label and the second label, and beads of interest retrieved. Finally, the identity of nucleic acid molecules which have a defined ratio of first and second label is determined.

In another aspect of the invention, relative amounts of transcript levels in cells are determined. For example, approximately equal amounts of mRNA or cDNA derived from two different cell or tissue types are labeled with two different markers, preferably fluorophores, and contacted with the bead having capture oligonucleotides attached to determine the relative expression levels of genes in the two samples. Differences in abundance are identified, and the relevant sequences are recovered and characterized. These differences may involve mRNAs/cDNAs that are overrepresented in one population as compared to the other.

In another aspect of the invention, genomic DNA derived from different sources is compared to identify copy numbers of specific chromosomal regions or loci, thereby identifying regions which are deleted or amplified, e.g., in samples derived from tumor tissue. In yet other aspects, genomic DNA fragments are linked to reporter genes to assess, for example, promoter activity of specific genomic DNA fragments in different cells.

Yet another strategy involves attachment of identifier tags to cloned DNA fragments. The identifier tags of the invention are selected to have minimal cross-hybridization activity. Typically, the identifier tags have the form of tandem multipliers of simpler sequence units of about two (2) to about fifteen (15) nucleotides in length, preferably of about seven (7) to about twelve (12), and more preferably of about seven (7) to about nine (9) nucleotides in length. In one preferred embodiment of the invention, sequence identifier tags comprise a combination of between two (2) and six (6) sequence units in tandem, each unit consisting of from about seven (7) to about fifteen (15) nucleotides. In a preferred embodiment of the invention, a family of identifier tags consists of a 24-mer, composed of combinations of three 8-mers. This population of 24-mers can be synthesized in 100 automated DNA synthesis columns using two stages of "split and recombine" synthesis. After completion of the last round of couplings, the result is a family of identifier tags comprising a degeneracy of about $1 \times 10^6$ ($100 \times 100 \times 100$). If the individual 8-mers are chosen propitiously, the greatest similarity among any two members of the family can be minimized. In cases where the target nucleic acids are linked to such identifier tags, the beads, as a variation, are synthesized with the "complements" of the above identifier tags as capture oligonucleotides.

An important aspect of the invention relates to methods for the determination of the relative abundance of individual cDNA (or genomic DNA) inserts in a genetic library, wherein the individual inserts are linked to unique identifier tags, which have been passaged through different cell types. This approach, referred to as "post-passage library comparison", permits identification and recovery of specific DNA sequences from the original library that are increased in abundance after passage through one cell type compared to the other. These sequences are candidates for genes or gene fragments that either selectively promote cell growth or inhibit cell growth.

In yet another aspect, the invention relates to methods for the normalization of cDNA libraries, i.e., a process to convert a cDNA library that represents different mRNAs according to their abundance in the cell into a library that represents the different mRNAs in roughly equal amounts.

Finally, the invention relates to methods for the recovery, identification and analysis of sequences that have a specific relative abundance in two populations of nucleic acid, e.g., MRNA, cDNA or genomic DNA.

BRIEF DESCRIPTION OF THE DRAWINGS

FIG. 7 depicts the concept of the "split and recombine" synthesis strategy for the generation of sequence identifier tags, as described in Example 8, infra.

FIG. 9 depicts the hybridization discrimination of identifier tags, as described in Example 10, infra.

DEFINITIONS

Figure 1:
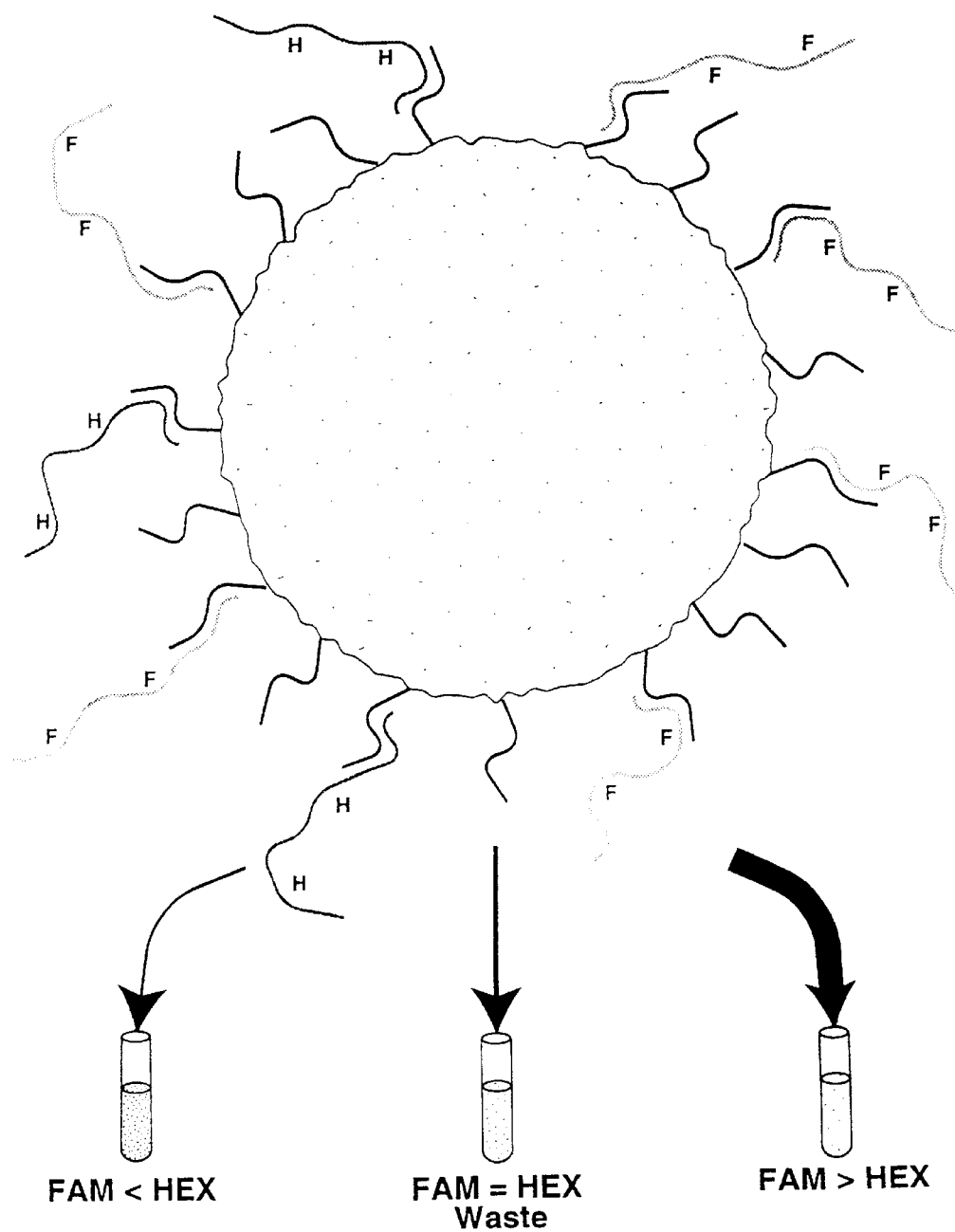
FIG. 1 depicts the FACS sorting of beads with labeled nucleic acids attached thereto, as described in Example 2, infra.

Terms used herein are in general as typically used in the art. The following terms are intended to have the following general meanings as they are used herein:

The term "complement" refers to a nucleic acid sequence to which a second nucleic sequence specifically hybridizes to form a perfectly matched duplex or triplex.

The term "cognate" refers to a sequence capable of forming a perfectly matched (see supra) duplex with its complement in the reaction mixture. "Non-cognate" refers to non-perfectly matched duplexes that may form—especially sequences that share very little in the way of complementary sequences to permit Watson-Crick base-pairing.

The term "oligonucleotide" includes linear oligomers of natural or modified monomers or linkages, including deoxyribonucleosides, ribonucleotides, a-anomeric forms thereof, further peptide nucleic acids, and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually, monomers are linked by phosphodiester bonds or analogs thereof to form oligonucleotides ranging in size from a few monomeric units, e.g., three (3) to four (4), to several tens of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphorandilidate, phosphoramidate, and the like. Usually oligonucleotides of the invention comprise the four natural nucleotides; however, they may also comprise non-natural nucleotide analogs. It is clear to those skilled in the art when oligonucleotides having natural or non-natural nucleotides may be employed, e.g., where processing by enzymes is called for, usually oligonucleotides consisting of natural nucleotides will be required.

The phrase "perfectly matched" in reference to a duplex means that the poly- or oligonucleotide strands of a duplex form a double-stranded structure with one other oligonucleotide strand such that every nucleotide in each strand undergoes Watson-Crick base pairing with a nucleotide in the other strand. The term also comprehends the pairing of nucleoside analogs, such as deoxyinosine, nucleotides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a base pair of the perfectly matched duplex.

A "mismatch" in a duplex between a tag and an oligonucleotide means that a pair or triplet of nucleotides in the duplex or triplex fails to undergo Watson-Crick and/or Hoogsteen and/or reverse Hoogsteen bonding. A single mismatch refers to a single non-Watson-Crick basepaired position in the duplex; a double mismatch refers to two mispaired bases, either in tandem or separated by one or more correctly paired positions; etc.

The term "nucleotide" includes the natural nucleotides, including 2'-deoxy and 2'-hydroxyl forms, analogs and derivatives thereof; further synthetic nucleotides having modified base moieties and/or modified sugar moieties, e.g., described by Scheit: *Nucleotide Analogs* (John Wiley New York, 1980); Uhlman and Peyman, 1990, *Chemical Reviews* 90:543–584, or the like, with the only proviso that they are capable of specific hybridization. Such analogs include synthetic nucleotides designed to enhance binding properties, reduce degeneracy, increase specificity, and the like.

A "linker" is a moiety, molecule, or group of molecules attached to a solid support, referred to as bead and spacing a synthesized polymer or oligomer, e.g., a oligonucleotide or other nucleic acid fragment, from the bead.

A "bead" refers to solid phase supports for use with the invention. Such beads may have a wide variety of forms, including microparticles, beads, and membranes, slides, plates, micromachined chips, and the like. Likewise, solid phase supports of the invention may comprise a wide variety of compositions, including glass, plastic, silicon, alkanethiolate-derivatized gold, cellulose, low cross-linked and high cross-linked polystyrene, silica gel, polyamide, and the like. Other materials and shapes may be used, including pellets, disks, capillaries, hollow fibers, needles, solid fibers, cellulose beads, pore-glass beads, silica gels, polystyrene beads optionally crosslinked with divinylbenzene, grafted co-poly beads, poly-acrylamide beads, latex beads, dimethylacrylamide beads optionally cross-linked with N,N$^1$-bis-acryloyl ethylene diamine, and glass particles coated with a hydrophobic polymer, etc., i.e., a material having a rigid or semirigid surface.

An "identifier tag" refers to a nucleotide sequence that can be attached via ligation or primed synthesis onto individual nucleic acid molecules, thus providing unique or almost unique means for identification and retrieval. For purposes of the invention, the length of an identifier tag is from about ten (10) to about ninety (90) bases and typically ranges from about ten (10) to about forty (40) bases.

The term "genetic library" refers to a collection of DNA fragments derived from mRNA, genomic DNA or synthetic DNA (non-natural DNA sequence) propagated in a vector that may be plasmid or virus based. The size of a genetic library may vary from a few individual inserts (or clones) up to many millions of clones.

The term "random sequence" refers to a set of nucleotide sequences of specified length such that the entire population encompasses every possible sequence of that length. Thus, a random sequence of length N contains $_4$N distinct individual sequences.

DETAILED DESCRIPTION OF THE INVENTION

A. Overview

The present invention relates to a method for the assessment of relative amounts of nucleic acid sequences in samples derived from a plurality of different sources. More specifically, the invention relates to a method using beads having attached to their surface unique oligonucleotides or nucleic acid fragments, collectively referred to as capture oligonucleotides or capture fragments, to select specific labeled nucleic acid sequences. A collection of a plurality of such beads, each linked to multiple copies of an oligonucleotide of unique sequence, are used to capture nucleic acids having a specific sequence to assess the relative abundance of specific nucleic acid sequences and to retrieve and analyze sequences with defined relative abundance.

More specifically, the methods of the invention may be used to compare quantitatively the amount of specific nucleic acid sequences in at least two samples derived from different sources, e.g., different cell or tissue types, different disease or developmental stages, and the like. Nucleic acids from the two samples are labeled in such a fashion that the signals can be distinguished and compared following hybridization to the capture oligonucleotides attached to the beads. Subsequently, the beads are sorted, e.g., by FACS analysis in cases where a fluorescent label is linked to the target nucleic acids, according to the ratio of the first label and the second label, which is indicative of the relative amounts of transcript contained in the two sources. The beads, along with the bound nucleic acid having a particular expression profile, are retrieved, and the nucleic acid is eluted and analyzed, for example by DNA sequence analysis.

B. Generation Of Beads Comprising Capture Oligonucleotides Or Nucleic Acids

Solid Supports/Beads.

The solid support materials to which the capture oligonucleotides or nucleic acids are attached are referred to herein as beads. Such beads may have a wide variety of shapes and may be composed of numerous materials, as defined, supra. Briefly, solid supports/beads used with the invention typically have a homogenous size between 1 and 100 microns, and include microparticles made of controlled pore glass (CPG), highly cross-linked polystyrene, acrylic copolymers, cellulose, nylon, dextran, latex, polyacrolein, and the like. See, among other references, *Meth. Enzymol.*, Section A, pages 11–147, vol. 44 (Academic Press. New York, 1976); U.S. Pat. No. 4,678,814; U.S. Pat. No. 4,413, 070. Beads also include commercially available nucleoside-derivatized CPG and polystyrene beads, e.g., available from Applied Biosystems, Foster City, Calif.; derivatized magnetic beads; polystyrene grafted with polyethylene glycol, e.g., TentaGel™, Rapp Polymerc, Tübingen Germany, and the like.

Selection of the bead characteristics, such as material, porosity, size, shape, and the like, and the type of linking moiety employed depends on the conditions under which the capture oligonucleotides are used. For example, in applications involving successive processing with enzymes, supports and linkers that minimize steric hindrance of the enzymes and that facilitate access to substrate, are preferred. Other important factors to be considered in selecting the most appropriate microparticle support include size, uniformity, efficiency as a synthesis support, degree to which the surface area is known, and optical properties, e.g., autofluoresence. Typically, a population of discrete particles is employed such that each has a uniform population of the same oligonucleotide or nucleic acid fragment (and no other). However, beads with spatially discrete regions each containing a uniform population of the same oligonucleotide or nucleic acid fragment (and no other), may be employed. In the latter embodiment, the area of the regions may vary according to particular applications. Preferably, such regions are spatially discrete so that signals generated by events, e.g., fluorescent emissions, at adjacent regions can be resolved by the detection system being employed.

In the preferred embodiments of the invention, beads are typically composed of glass, plastic, or carbohydrate, and have chemical and spectral properties appropriate for their use in nucleic acid attachment and fluorescent activated cell sorter (FACS) analysis. For example, if they are used with chemical synthesis of oligonucleotides, they must withstand prolonged exposure to organic solvents such as acetonitrile. They can be chemically derivatized so that they support the initial attachment and extension of nucleotides on their surface. The beads also will possess autofluorescence profiles and mass densities that permit their use on a FACS machine. In general, the solid support may be composed of some form of glass (silica), plastic (synthetic organic polymer), or carbohydrate (sugar polymer). A variety of materials and shapes may be used, including beads, pellets, disks, capillaries, hollow fibers, needles, solid fibers, cellulose beads, pore-glass beads, silica gels, polystyrene beads optionally crosslinked with divinylbenzene, grafted co-poly beads, poly-acrylamide beads, latex beads, dimethylacrylamide beads optionally cross-linked with N,N$^1$-bis-acryloyl ethylene diamine, glass particles coated with a hydrophobic polymer, etc., i.e., a material having a rigid or semirigid surface.

Attachment Of Capture Oligonucleotides To Beads: Linker Chemistry.

Capture oligonucleotides may be synthesized directly on the bead upon which they will be used, or they may be separately synthesized and attached to a bead for use, e.g. as set forth in Lund et al., 1988, *Nucleic Acids Research* 16:10861–10880; Albretsen et al., 1990, *Anal. Biochem.* 189:40–50; Wolf et al., 1987, *Nucleic Acids Research* 15:2911–2926; and Ghosh et al., 1987, *Nucleic Acids Research* 15:5353–5372.

The oligonucleotides may be attached to the beads using a variety of standard methods. Conveniently, the bond to the bead may be permanent, but a linker between the bead and the product may also be provided which is cleavable such as exemplified in Example 1. Exemplary linking moieties for attaching and/or synthesizing tags on microparticle surfaces are disclosed in, e.g., Pon et al., 1988, *Biotechniques* 6:768–775; Webb, U.S. No. Pat. 4,569,774; Barany et al. PCT Patent Application PCT/US91/06103; Brown et al., 1989, *J. Chem. Soc. Commun.* __:891–893; Damba et al., 1990, *Nucleic Acids Research* 18:3813–3821; Beattie et al., 1993, Clinical *Chemistry* 39:719–722; Maskos and Southern, 1992, *Nucleic Acids Research* 20:1679–1684.

Desirably, when the product is permanently attached, the link to the bead will be extended, so that the bead will not sterically interfere with the binding of the product during screening. Various links may be employed: including hydrophilic links, such as polyethyleneoxy, saccharide, polyol, esters, amides, saturated or unsaturated alkyl, aryl, combinations thereof, and the like.

Functionalities present on the bead may include hydroxy, carboxy, iminohalide, amino, thio, active halogen (Cl or Br) or pseudohalogen (e.g., —CF$_3$, —CN, etc.), carbonyl, silyl, tosyl, mesylates, brosylates, triflates or the like. In some instances the bead may have protected functionalities which may be partially or wholly deprotected prior to each stage, and in the latter case, reprotected. For example, amino acids may be protected with a carbobenzoxy group as in polypeptide synthesis, hydroxy with a benzyl ether, and the like.

In some cases, detachment of the capture oligonucleotide may be desired and there are numerous functionalities and reactants which may be used for detaching. Conveniently, ethers may be used, where substituted benzyl ether or derivatives thereof, e.g., benzhydryl ether, indanyl ether, and the like may be cleaved by acidic or mild reductive conditions. Alternatively, one may employ β-elimination, where a mild base may serve to release the product. Acetals, including the thio analogs thereof, may be employed, using mild acid, particularly in the presence of a capturing carbonyl compound. By combining formaldehyde, HCl and an alcohol moiety, an α-chloroether is formed. This is then coupled with an hydroxy functionality on the bead to form the acetal. Various photolabile linkages may be employed, such as o-nitrobenzyl, 7nitroindanyl, 2-nitrobenzhydryl ethers or esters, and the like. Esters and amides may serve as linkers, where half-acid esters or amides are formed, particularly with cyclic anhydrides, followed by reaction with hydroxyl or amino functionalities on the bead, using a coupling agent such as a carbodiimide. Peptides may be used as linkers, where the sequence is subject to enzymatic hydrolysis, particularly where the enzyme recognizes a specific sequence. Carbonates and carbamates may be prepared using carbonic acid derivatives, e.g., phosgene, carbonyl diimidazole, etc. and a mild base. The link may be cleaved using acid, base or a strong reductant, e.g., LiAlH$_4$, particularly for the carbonate esters.

If the capture oligoncucleotides are chemically synthesized on the bead, see, infra, the bead-oligo linkage must be stable during the deprotection step. During standard phosphoramidite chemical synthesis of oligonucleotides, a succinyl ester linkage is used to bridge the 3' nucleotide to the resin. This linkage is readily hydrolyzed by NH$_3$ prior to and during deprotection of the bases. Thus, the finished oligonucleotides are released from the resin in the process of deprotection.

In specific embodiments of the invention, the capture oligonucleotides are linked to the beads (1) via a siloxane linkage to Si atoms on the surface of glass beads; (2) a phosphodiester linkage to the phosphate of the 3'-terminal nucleotide via nucleophilic attack by a hydroxyl (typically an alcohol) on the bead surface; or (3) a phosphoramidate linkage between the 3'-terminal nucleotide and a primary amine conjugated to the bead surface.

In a first embodiment, glass beads are treated with 3-glycidoxypropyltrimethoxysilane to generate a terminal epoxide conjugated via a linker to Si atoms on the glass. In a second step, the expoxide is opened with either water or a diol to generate alcohols. Maskos and Southern, 1992, *Nucleic Acids Research* 20:1679–1684. The resulting siloxane linkage is relatively stable to base hydrolysis. Glass beads are a necessary starting material to produce hydroxyl groups suitable to begin cycles of phosphoramidite chemistry in a conventional automated DNA synthesizer. In some preferred applications, commercially available controlled-pore glass (CPG) or polystyrene supports are employed as beads. Such supports are available with base labile linkers and initial nucleosides attached, by, e.g., Applied Biosystems (Foster City, Calif.). Alternatively, non-porous glass beads, e.g., Ballotini spheres are employed (Maskos and Southern, 1992, *Nucleic Acids Research* 20:1679–1684).

In a second embodiment, the linkage is created by the reaction of primary amines with phosphoramidite nucleotides to produce a base-stable linkage. Pon et al., 1988, *Biotechniques* 6:768–775. In the first step of the reaction an N-P linkage is formed due to nucleophilic attack by nitrogen on phosphorus. This linkage is oxidized in a subsequent step to the phosphoramidate, a stable chemical linkage. Beads that are functionalized with surface primary amines can be obtained from commercial sources.

In a third embodiment, the capture oligonucleotides are attached to the bead via a phosphodiester bond generated by standard phosphoramidite synthesis utilizing the attack of bead-linked hydroxyl oxygens on the nucleotide phosphorus to produce a phosphodiester bond, following oxidation with molecular iodine. Others have utilized this reaction to generate stable linkages (e.g., Needels et al., 1993, *Proc. Natl. Acad. Sci. U.S.A*. 90:10700–10704). The key step is the derivatization of appropriate beads such that they contain significant numbers of hydroxyl functional groups on their surface. It is possible to purchase such functionalized beads from a variety of commercial sources; the capture oligonucleotides may be synthesized chemically on the surface of these functionalized beads.

Generally, standard synthesis chemistries are used, such as phosphoramidite chemistry, as disclosed in Beaucage and Iyer, 1992, *Tetrahedron* 48:2223–2311, Molko et al., U.S. Pat. No. 4,980,460; Koster et al., U.S. Pat. No. 4,725,677; Caruthers et al., U.S. Pat. Nos. 4,415,732; 4,458,066; and 4,973,679. Alternative chemistries, e.g., resulting in nonnatural backbone groups, such as phosphorothionate, phosphoroamidate, and the like, may also be employed, provided that the resulting capture oligonucleotides are capable of specific hybridization.

As described in Shortle et al., PCT Application PCT/US93/03418, phosphoramidite chemistry may be used. 3' phosphoramidite oligonucleotides are prepared according to standard procedures described. Synthesis proceeds as disclosed by Shortle et al., or in direct analogy with the techniques employed to generate diverse oligonucleotide libraries using nucleosidic monomers, e.g., as disclosed in Telenius et al., 1992, *Genomics* 13:718–725; Welash et al., 1991, *Nucleic Acids Research* 19:5275–5279; Grothues et al., 1993, *Nucleic Acids Research* 21:1321–1322; Hartley, European Patent Application No. 90304496.4; Lam et al., 1991, *Nature* 354:82–84; Zuckerman et al, 1992, *Int. J. Pept. Protein Res*. 40:498–507. Generally, these techniques call for the application of mixtures of the activated monomers to the growing oligonucleotides during the coupling process.
Oligonucleotide Extension/Amplification Strategy.

A prerequisite of the invention disclosed herein is that each individual bead have many copies of one, and preferably only one, and no more than a few, unique capture oligonucleotide or nucleic acid sequences displayed on its surface. This can be achieved in a variety of ways.

In one embodiment of the invention, the capture oligonucleotides are synthesized by constraining the PCR to the surface of the beads. For example, the beads may be coated with two amplification primers, one "forward" primer and a "reverse" primer, which are complementary to a target nucleic acid sequence. In solution, these two primers are capable of amplifying the target nucleic acid. When these primers are on a bead coupled via their 5' ends they are not freely diffusible in solution. These primers will prime synthesis of new molecules while attached to the bead. Thus, potential template molecules must diffuse to the bead and anneal to the attached primer(s). When this happens, a complementary strand can be synthesized on the template using a DNA polymerase exactly as the reaction occurs during normal solution phase PCR. Following extension of the new strand, denaturation releases the original template molecule, but leaves the newly synthesized strand attached to the bead via its priming oligonucleotide. In a second round of annealing and extension, the new strand can fold back onto the bead surface to hybridize with the reverse primer forming a bridge. This bridge can be converted into double-stranded DNA by a further round of extension with a polymerase. The denaturation step results in two complementary single strands attached to the bead, one derived from the forward primer, the other one from the reverse. In subsequent rounds of amplification, the two strands reanneal with other primers on the bead's surface. If a single template molecule begins the amplification on a given bead, and if the Watson strands are released by selective hydrolysis of the Watson primer linker for example, the bead ends up covered by many copies of a single sequence (within the limits of PCR). This method could be used to generate a family of beads, each having a unique sequence representing, for instance, a clone from a cDNA library. In this embodiment, unique nucleic acid fragments attached to a solid support, such as a bead, may have a length of from about 50 to about 5,000 nucleotides.

In preferred embodiments, the family of beads each with a single type of capture oligonucleotide sequence attached to its surface is created by chemical synthesis in a "split synthesis" mode. More specifically, a population of beads with capture oligonucleotides of arbitrary length and random sequence is generated as follows: A collection of beads numbering in the millions is split into four groups designated (a), (c), (g), and (t). Each group serves as the basis for deposition of the first nucleotide, which is different for all groups. Thus, group (a) receives an adenosine moiety, group (c) receives a cytosine, group (g) receives a guanosine, and group (t) receives a thymidine. Following completion of the first synthesis step the four groups of beads are pooled into a common pot, mixed and redistributed (split) into each of the four initial groups. Thus, one quarter of group (a) is left in the original group's location, one quarter is mixed with the remaining quarter of group (c), one quarter with group (g), etc. A second round of synthesis is then completed placing an adenosine on the beads in the group (a) location, a cytosine on the beads in the group (c) location, etc. This process can be repeated several times to generate a population of beads that, overall, has random sequence (equal amounts of A, C, G and T at each base position), but with each bead having a homogenous population of capture oligonucleotides on its surface. See, FIG. 6. The subdivision and reassortment of beads during synthesis can be varied to skew the population of beads away from a random sequence distribution. The number of bases per oligonucleotide (a constant for each synthesis) can be varied from synthesis to synthesis. Using this approach, oligonucleotides of a determined length, typically between approximately ten (10) and fifty (50) nucleotides long, preferably between approximately ten (10) and forty nucleotides long may be produced. In one preferred embodiment of the invention, oligonucleotides between approximately ten (10) and twenty (20) nucleotides long are produced. In another preferred embodiment of the invention, capture oligonucleotides having a length of from about twelve (12) to about thirty (30) nucleotides and which comprise a stretch of from about 10 to about 20 nucleotides of random sequence are produced. In yet another preferred embodiment of the invention, 24-mers composed of three 8-mer units are produced. As an alternative, a defined sequence of a desired number of bases may be added to the growing capture oligonucleotide attached to the surface of the beads at any stage in the synthesis. Thus, the capture oligonucleotides may contain certain regions of identity and certain regions of known distinguishable sequence.

In some cases it is desirable to generate beads with capture oligonucleotides that are not random in sequence, yet nonetheless contain among them a considerable degree of diversity. This is accomplished by parallel chemical syntheses. However, when a high diversity of capture oligonucleotides is desired, this becomes extremely expensive and labor-intensive with current technology. However, as provided by the present invention, a combinatorial diversity may be generated by a modified "pool and split" synthesis approach. See, FIG. 7. For example, with this approach two split and recombine steps on one hundred (100) synthesis columns would produce one million different 24-mers. Specifically, in a first series of couplings, one hundred (100) columns are used to synthesize one hundred (100) different 8-mers that remain attached to the beads in each column. After the eighth coupling round, the contents of each column are pooled and redistributed (split) into one hundred (100) new columns. Thus, all combinations of the contents of the one hundred (100) columns are generated, with a final number of columns again equal to one hundred (100). Eight further couplings are completed in these new columns, each column receiving a unique series of couplings. This second set of couplings generates 16-mers (eight plus eight) in one hundred (100) columns, with a population diversity of ten thousand (10,000). After an additional "pool and split" operation on the column contents into the final set of one hundred (100) columns, eight further couplings are completed. This results in a final product of one million different bead types, each with many copies of a unique 24-mer. Note that no bead type contains a sequence that is any more similar than the similarity between one of the 8-mers. Thus, each sequence can be chosen to differ from any other sequence in principle, by several mismatches. This drastically improves the specificity of the capture oligonucleotides.

C. Identifier Tags

Some of the specific applications disclosed herein rely on "tracking" of specific individual nucleic acid molecules. This can be accomplished by attaching sequence identifier tags to each individual nucleic acid sequence comprising a mixture.

Sequence identifier tags are unique oligonucleotide sequences that allow identification and recovery of specific sequences in a complex population of target nucleic acids. For example, in the case of a cDNA library that contains one million individual clones, it is optimal to construct the library such that each clone possesses its own unique identifier tag.

In order to minimize the background signal, it may be necessary for the identifier sequences to be designed in such a way that cross hybridization is minimized. This can be accomplished by synthesis of oligonucleotides which are composed of pluralities of "units". Generally, such "units" range in size from about (2) to about thirty (30) nucleotides, preferably from about two (2) to about twelve (12) nucleotides, and may be synthesized using the above described "split/recombine" synthesis method. In one preferred embodiment of the invention, sequence identifier tags comprise a combination of between two (2) and six (6) sequence units in tandem, each unit consisting of from about seven (7) to about fifteen (15) nucleotides. The total length of the oligonucleotide may thus vary from about fourteen (14) to about ninety (90) nucleotides.

Units in the range of from about seven (7) to about nine (9) nucleotides are preferred, as they provide a perfect compromise between the complexity which can be achieved and inherent specificity. For example, using one hundred (100) synthesis columns in a split/recombine synthesis approach, a mixture of 24-mers composed of three 8-mer units will have a complexity of $1 \times 10^6$, see, supra. Thus, while high complexity can readily be achieved, the final 24-mer oligonucleotides can be hybridized with reasonably high specificity, as each individual oligonucleotide should differ from the other 24-mers in the population by several mismatches, preferably in at least eight (8) positions. Thus, there should be minimal cross-hybridization. The length of the perfectly matched hybrids, 24 basepairs, also permits relatively high temperatures to be used for hybridization and washing. This characteristic is valuable in promoting more rapid hybridization reaction and increased specificity. A related concept for the generation of oligonucleotide identifier tags which exhibit minimal cross hybridization is disclosed in Brenner, PCT Patent Application Nos. PCT/US95/12791, PCT/95/03678, and PCT/95/12678, hereby incorporated by reference in their entirety. Specifically, Brenner discloses oligonucleotide tags consisting of a plurality of subunits three to six nucleotides in length selected from a minimally cross-hybridizing set. Although the identifier tags provided by Brenner may be used for the methods of the present invention, slightly longer units, as discussed above, ranging from seven (7) to nine (9) base pairs are preferred for applications specifically disclosed herein.

Generally, oligonucleotides are synthesized using standard techniques, see, supra, Section VI.B. In many instances, the oligonucleotide tags of the invention may be conveniently synthesized on an automated DNA synthesizer, e.g., an Applied Biosystems, Inc. (Foster City, Calif.) model 392 or 394 DNA/RNA synthesizer, using the above described and referenced standard chemistries. See, Section VI.B.

Attachment Of Tags To DNA Or cDNA.

Many approaches known to the skilled artisan may be used to attach the identifier tags onto genomic or cDNA. In the following, preferred methods are described.

One preferred method employs a first strand cDNA primer which is composed of three distinct segments. Specifically, the 3' end of the primer contains a random sequence, e.g., a hexamer, followed by a segment comprised of a defined number of "units" of defined length (e.g. three 8-mer units, corresponding to the 24-mers described above), and, optionally, a constant sequence segment containing a restriction endonuclease recognition sequence. The resulting first strand primer thus has a length of about thirty (30) to fifty (50) base pairs, with a random 3' segment as a means for randomly primed cDNA synthesis, followed by, e.g., a one million fold degenerate 24mer as identifier tag, and an optional 5' sequence shared among all primers containing a restriction endonuclease recognition sequence useful in cloning. Alternatively, if oligo(dT)-primed synthesis is desired, the primer contains 8–16 T's at its 3' end instead of the random hexamer.

Such a first strand primer is used to reverse transcribe the first stand of cDNA from MRNA (or polymerize on genomic DNA) prepared from a source of interest under conditions suited for randomly primed synthesis. The first cDNA strand is then converted into second strand cDNA in such a fashion that it can be directionally cloned in a plasmid or phage vector. Cloning techniques generally known in the art are employed. See, e.g., Sambrook et al., supra. Briefly, the cDNA is ligated to the vector, either using specific sticky end restriction endonuclease sites (in cases where such restriction enzyme recognition sequences are included at the 5' end of the first strand synthesis primer), or by blunt end subcloning. Typically, the phage or plasmid vector contains a selectable marker. The plasmids are transformed into suitable bacterial cells, e.g., E. coli and clones are selected. The library of clones, typically numbering at least one million independent colonies or plaques, are expanded and DNA is isolated. The obtained DNA then serves as the template for subsequent amplification by PCR using either generic primers present in the original cDNA material (e.g., the constant region at the 5' end of the random primers), or from flanking vector sequences. The amplified cDNA now contains representatives from roughly one million clones, each labeled with a unique (or nearly unique) tag, e.g., the attached 24-mer.

In an alternative embodiment, sequence identifier tags are attached by ligation of linker DNA molecules onto the ends of genomic DNA fragments or cDNAs. Several possible methods could be employed. One specific example involves ligation of a vector (e.g., a plasmid) that contains the identifier sequence tags flanking the cloning site. The population of cloning vector molecules is itself degenerate, since there are, e.g., one million different sequences (corresponding to the one million identifier tags) represented among them. After ligation, e.g., of genomic DNA inserts, prepared, e.g., by random shearing, into the vector population and transformation into E. coli host cells, a set of library clones can be isolated, each of which contains a unique or nearly unique identifier sequence attached to it.

D. Labeling The Target Nucleic Acid

In accordance with the invention, the target nucleic acids are labeled with a marker, preferably a visual marker, including chromophores, fluorophores and the like.

In preferred embodiments, the target nucleic acid is labeled with fluorophores to permit detection by instruments like the automated fluorescence activated cell sorter (FACS) or cell scanner. Such machines allow quantitative measurement of fluorescence signals in multiple channels (i.e., at multiple wavelengths) and can compute fluorescence intensity ratios at different wavelengths; typically the range runs between 400–600 nm. Designed to measure fluorescence in cells or on cell surfaces, the machines can be readily adapted to monitor fluorescence on beads of various types.

Fluorophores can be attached to the nucleic acid in many ways. For example, PCR primers, labeled at their 5' ends with, e.g., a fluorophore such as HEX or FAM, may be used to generate amplified fragments that are labeled at one end with the fluorophore of interest. The amplified material is the target nuclei acid. It can be rendered single stranded such that the remaining single strands contain the fluorophore, and can be used for hybridization to probe sequences on beads.

Alternatively, the fluorophores may be coupled to nucleic acid molecules by ligation of labeled linkers, by incorporation of labeled nucleotides via polymerases, or possibly by more nonspecific chemical reactions. A further alternative involves incorporation of modified bases that can be bound by a fluorophore-containing ligand, e.g., biotinylated bases that can be bound with fluorophore-conjugated avidin.

E. Hybridization Of Probes And Target Nucleic Acids

Hybridization and washing conditions for the experiments described below are critical. The conditions have to be such that they promote the formation of perfectly matched duplexes between the probes, i.e., the capture oligonucleotides attached to the beads, and the target, i.e., the nucleic acid molecule complements in the samples. There is extensive guidance in the literature for creating these conditions. Exemplary references providing such guidance include Wetmur, 1991, *Critical Reviews in Biochemistry and Molecular Biology* 26:227–259; Sambrook et al., Molecular Cloning: A Laboratory Manual, 2nd Edition (Cold Spring Harbor Laboratory, New York, 1989): and the like. Preferably, the hybridization conditions are sufficiently stringent so that only perfectly matched sequences form stable duplexes.

Relevant issues for choosing the hybridization conditions include the specificity or selectivity of the hybridization and the sensitivity of the method. The issue of specific hybridization and its optimization has been described and analyzed in great detail in Brenner, PCT Application PCT/US95/12791. As with many physical measurement processes, a key concept is the signal to noise ratio of the procedure. The signal to noise ratio for a hybridization experiment such as the ones described herein can be estimated by theory, incorporating base composition of the hybridizing sequences, length of sequences, salt concentration of the hybridization buffer, temperature, and the like. Generally, such calculations permit a rough estimate to be obtained which must be refined for practical reasons by a series of empirical measurements. For example, a specific sequence can be doped into the mixture of nucleic acids, along with appropriate cognate beads. A variety of hybridization and washing conditions can be examined, where the readout is the specific fluorescence signal on the cognate beads, compared with the signal on noncognate beads. The goal of this procedure is to arrive at conditions where the ratio of the cognate signal to the noncognate signal is maximal. The parameters that are most easily manipulated are temperature and salt concentration. Low stringency of hybridization involves high salt and/or low temperatures. High stringency, conversely, involves low salt and/or high temperatures. It is also possible to carry out a first wash at a relatively nonstringent condition, followed by a FACS analysis. The flow through beads can then be rewashed under more stringent conditions prior to another FACS experiment. In this way, the fluorescence intensity ratios of the beads can be examined under two or more conditions and individual beads can be culled from the population according to desired ratios under these different conditions.

Sensitivity is understood to be the minimum amount of real target nucleic acid that can be detected reliably on the bead surface. For example, a bead that should selectively bind sequence X, will reveal progressively lower signals for X as the concentration of X is reduced. In the case of FACS analysis, the amount of X on the bead is measured by X-specific fluorescence.

Selectivity is understood to be the ability of the X-specific bead to bind X (cognate sequence) as opposed to other non-X sequences (non-cognate sequence) presented during hybridization. For example, if X is mixed with sequence Y in different proportions, and each is labeled with the same chromophore, the degree of selectivity determines the ratio of X-signal to Y-signal on an X-specific bead following hybridization and washing. The limit of the sensitivity is the point at which the X-signal is no longer detectable above the background noise caused by hybridization of Y. The limit of sensitivity depends on both the amount of hybridized X on the bead, and the amount of non-specific binding of Y on the bead. The signal to noise issue in the context of hybridization experiments is best formulated in terms of chemical equilibrium, as it is defined by the difference in binding energies under certain conditions between X and Y to the X-beads. If the difference is, e.g., 4.2 kcal/mole, at equilibrium 1000 fold more X should be bound than Y.

Another key issue in the hybridization process relates to the rate at which X hybridizes to the X-bead. This rate depends on numerous factors, two of the most important being the concentration of X in solution, and the number of X-specific capture oligonucleotides attached to the bead surface. In reactions where X is present in vast excess, the reaction can be thought to proceed in a pseudo-first order manner, that is, the concentration of X changes little as the capture oligonucleotides on the bead anneal to the X molecules. Under the conditions of the methods of the invention, the reaction proceeds according to second order kinetics because X is present at low concentration, i.e., at a fraction of the total target nucleic acid that is presented in the hybridization reaction.

Hybridization reactions that involve one hybridizing species immobilized to a surface behave slightly differently from the ideal chemical reaction involving complex formation between two freely diffusible reactants. Nevertheless, it is useful to consider the concentrations of the hybridizing species, the capture oligonucleotides on the bead surface and the target nucleic acid in solution, to help understand the utility of the present invention.

To maximize the signal to noise ratio, it is preferred to choose hybridization conditions that permit maximum binding of the specific hybridization target sequence, and minimize the binding of the nonspecific target sequences. Nucleic acid hybridization is a complex process that depends on a variety of factors, including sequence composition and length, ionic strength, pH, and temperature. Propitious choice of the identifier tags is a first step in achieving a good signal to noise ratio. The tag sequences should be chosen such that each one has roughly the same G/C content as every other. In addition, secondary structure in the tags should be minimized by design. Once the sequences are selected, other variables such as salt concentration and temperature can be tested for hybridization and washing so that the signal to noise ratio is maximized.

The kinetics of the process is critical. In order to detect rare molecular species in the target nucleic acid mixture, it is necessary to include high concentrations of target and/or probe in the reaction, and/or let the reaction proceed for a long time. Indeed the product of initial concentrations of the reaction species and the time of reaction (the "Cot") is a key parameter that must be considered. A reasonable limit for hybridization time is 24 hours. It is often not practical to wait longer than one day for the hybridization reaction to proceed. In addition, there is a limit as to the concentration of DNA that can be manipulated in solution, typically not more than 10 mg/mi.

In the case where the two hybridizing species are diffusible, a rough formula for predicting the rate of the reaction is given by:

$$(1/X)(Y/5)(Z/10) \times 2 = \text{number of hours to achieve Cot}_{1/2} \text{ (50\% formation of duplex)},$$

where X=mass of nucleic acid sequence in micrograms,
where Y=complexity of nucleic acid sequence in kilobases (complexity usually is the length of the sequence),
and where Z=volume of the reaction in milliliters.

Thus for a reaction that involves $10^{11}$ Watson molecules and $10^{11}$ Crick molecules of 500 basepairs in length in a reaction volume of 10 microliters, $\text{Cot}_{1/2}$ is expected to be reached in about 4 hours. If, however, one of the complementary molecules, e.g., the Crick species, is attached to a solid support, this calculation is not necessarily valid. To compensate for the lack of diffusibility of the bead-conjugated species, the sample must be continuously mixed. If the mean mixing velocity is comparable to the mean diffusion velocity of Crick molecules in the reaction, the reaction rate can be approximated by the same equation given above. A more rigorous treatment must include other aspects of the reaction, e.g., the fact that the bound nucleic acid molecules have fewer degrees of freedom than molecules in solution. Longer linker sequences can be added to separate the hybridizing oligonucleotide sequences from the bead surface to improve reaction rates if necessary (Lund et al., 1988, *Nucleic Acids Res* 16:10861–10880; Day et al., 1991, *Biochem J* 278:735–740).

1. The Capture Oligonucleotide Attached To The Bead As Probe

The probe consists of immobilized DNA, referred to as capture oligonucleotide or nucleic acid fragment, on the surface of a bead. The absolute number of DNA molecules that can be attached to the bead depends on many factors. However, it is unlikely to exceed a density determined by the available surface area on a microsphere of radius. If the beads have a 10 micron radius, their surface area is roughly 1200 square microns (=$1.2 \times 10^{11}$ Å$^2$). The approximate width of an aromatic ring is 6 Å. Thus, typically, the capture oligonucleotides onto the surface are spaced not closer than 6 Å, even if an alkyl linker is used. At an intermolecular spacing of 6 Å, the number of capture oligonucleotides that can be attached onto the surface of a 10 micron radius bead is about $3 \times 10^9$. In the extreme case, a hybridization reaction may involve a single bead with approximately one billion capture oligonucleotides attached to its surface. For example, if the reaction takes place in about 1 ml hybridization solution, the molarity of the specific oligonucleotide in solution is only on the order of $1 \times 10^{-12}$ M. This can be increased either by using a smaller hybridization volume, or by using a larger bead. For example, a bead that is twice the size of the 10 micron bead, could accommodate four times as many capture oligonucleotides on its surface.

2. The Target

The target nucleic acid is free in solution. We assume that the uppermost level of permissible nucleic acid concentration is about 10 mg/ml, which corresponds to a molarity of 32 µM for fragments of an average size of 500 bp (duplex). Accordingly, in nonrepetitive mammalian DNA, at a DNA concentration of 10 mg/ml an individual 500 bp fragment is present on the order of about $1 \times 10^{-11}$ M. In a population of one million cDNA clones, each about 500 nucleotides long, the concentration of each individual clone is essentially the same, i.e., about $1 \times 10^{-11}$ M.

The nonrepetitive fraction of denatured mammalian DNA at a concentration of 10 mg/ml will largely reassociate within a period of one day (or thereabouts). In this case, each hybridizing species (Watson and Crick) is present at about $1 \times 10^{-11}$ M. Therefore, it is reasonable to expect that the capture oligonucleotides attached to the bead and a target population of cDNA with complexity of about one million 500 bp fragments will also reassociate in the same time period. By reassociation is meant the formation of duplex in about half of the initial single-stranded species, not complete elimination of all single-stranded reactants.

3. Detection Limits

It would be ideal to detect signals from target nucleic acid hybridized to beads at a level of one in a million, which would correspond to detection of one specific cDNA fragment among one million others. The sensitivity of the method depends, as discussed above, on numerous factors. A FACS machine cannot detect the signal from fewer than 1,000–10,000 fluorophores. Thus, the reaction must proceed sufficiently towards completion such that this minimum number of target fluorophores becomes annealed to the correct bead. In addition, the background, i.e., nonspecific signal must also be considered. The experiments of Schena et al., supra, suggest that a detection sensitivity of better than one in 10,000–100,000 is readily achievable.

To increase detection sensitivity, the hybridization reaction may be split into several parts. For example, if the 24-mer identifier tags are used, they can be apportioned into 100 different tubes (wells) for independent hybridization. After the final coupling series of 8-mers to generate the set of one million 24-mers, the beads from each of the synthesis columns are transferred to a hybridization plate with 100 wells; thus each well has only 10,000 bead types, rather than one million. A cDNA library containing the one million tagged cDNAs is then amplified in one hundred parallel PCR reactions, each reaction using a different 10,000 fold degenerate subset of the 24-mers. The amplified library material is then dispensed into the appropriate bead-containing well for hybridization. Thus, the complexity of the reaction is reduced by two orders of magnitude, to increase both the kinetics of the reaction and the signal to noise ratio of the subsequent detection procedure, e.g., where the hybridized beads are passed through a FACS machine, as described below.

4. Enrichment, Recovery and Analysis

In preferred embodiments of the invention, the target nucleic acids are labelled with a fluorophore, and the detection and sorting process is done by means of a fluorescence activated cell sorter (FACS). See, supra, Section VI.D. However, the skilled artisan will appreciate that many other means will fulfill the same purpose.

FACS machines can sort beads at a rate of about 100 million per hour. This is done in series, but it is so rapid that is competes effectively with procedures that can be performed in parallel. It is also possible to sort beads based on one criterion, and then re-sort based on another. For example, sorting of fluorescence intensities within a prescribed window could be carried out twice to improve accuracy, if necessary.

The beads are forced through a nozzle, having a diameter of typically between 70 and 400 microns, at high pressure. Tiny liquid droplets are formed at the nozzle spout that occasionally contain individual beads. These water droplets are accelerated in one direction or another based on a droplet charge that responds to a variable electrostatic field across the nozzle stream. Actuation of the field automatically allows beads with particular parameters, e.g., size or fluorescence, to be sorted into, typically, one of three different tubes.

As the method of the invention comprises the comparison of relative levels of nucleic acids derived from two (or more) sources, the two target nucleic acid populations are typically labeled with dyes whose emission peaks are separable with the instrument. See, supra, Section VI.D. For instance, standard ABI fluorescent dyes, Hexachloro-Fluorescein (HEX), 6-carboxy-Fluorescein (FAM), Tetrachloro-Fluorescein (TET), Tetramethyl-6-carboxyrhodamine (TAMRA), 6-carboxy-X-rhodamine (ROX), 6carboxy-2', 7'-dimethoxy-4', 5'-dichlorofluorescein (JOE), 5-carboxyfluorescein (5FAM), and 6-carboxyrhodamine (R110) may be used. This dye set is available commercially from the Applied Biosystems Division of Perkin-Elmer (Foster City, Calif.). These and numerous other fluorophores compatible with DNA labeling, such as phycoerythrin, are also available from other commercial sources and have sufficiently different emissions spectra that a standard FACS can measure their intensities, and calculate a ratio. The user can choose the ratio which provides the most useful basis for sorting the beads, according to the desired parameters. Accordingly, for the purposes of sorting beads based on specific characteristics of the hybridized target nucleic acid, e.g., the ratio of nucleic acids labelled with different fluorophores, a preferred instrument is one that can determine fluorescence intensity in at least two wavelength channels, essentially simultaneously, as a bead-containing droplet passes through the laser beam on its way along the nozzle stream course. In addition, an "on-the-fly" computation must be performed such that the fluorescence in two channels is compared as, e.g., a ratio of two colors.

In addition, beads that satisfy the sorting criteria can be recovered and the annealed nucleic acid, suitably prepared with procedures known in the art (Hattier et al., 1995, *Mammalian Genome* 6:873–879) can be used as a template in PCR reactions. Optionally, the re-amplified material may be rehybridized to beads in order to provide a second (or third, etc.) round of enrichment. This aspect of the invention may be valuable in particular for the recovery of fragments derived from cDNA libraries that have been passaged through cells. See, infra. Briefly, the passaged cDNA fragments are quantified by hybridization to beads followed by FACS sorting based on relative fluorescence, are thenre-amplified, and re-introduced into cells. This provides a mechanism for achieving multiple rounds of enrichment, recovery, and repassage, which allows amplification of differences in gene expression, and thus increases the sensitivity of the system.

There are a variety of methods known in the art for the determination of the nature of the bead/capture oligonucleotide that has been recovered. Baum, 1996, *Chemical & Engineering News Feb.* 12 Issue:28–64. For instance, organic molecules may be used to tag the synthesis of combinatorial chemical reactions and provide the basis for subsequent reading of the beads by gas chromatographic detection. Alternatively, the beads may contain a radiographic bar code that identifies the nature of the bound material. In yet another approach, the nature of the capture oligonucleotide sequence attached to the bead is determined by PCR using primer binding sites of known sequence that flank the variable portion.

In yet another alternative, it may be preferable to bypass determination of the capture oligonucleotide sequence attached to each bead, and concentrate only on the target nucleic acid annealed to the bead. This can be accomplished by simply eluting the target sequence under conditions where a single bead can be isolated. This might be accomplished by limiting dilution or by specialized robotic attachment. PCR using known primers that flank the target fragments permits amplification. Depending on whether or not the bound material is homogeneous to a satisfactory degree, it may be necessary to clone the amplified fragments prior to DNA sequence analysis. If the bound target nucleic acid is predominantly of one type, e.g., a single cDNA clone fragment, readable DNA sequence may be obtained immediately without an intervening cloning step.

F. Normalizing Libraries or Populations of Nucleic Acids

The bead hybridization methodology readily permits normalization of cDNA libraries. Normalization is a process to convert a cDNA library that represents different mRNAs in the cell according to their natural abundance, into a library that represents different mRNAs in roughly equal amounts. For example, a typical mammalian cell has about 500,000 individual mRNA molecules representing a total of about 10,000 expressed genes. Some genes such as actin produce large quantities of message, exceeding in some cases 5,000 copies per cell. Other genes, however, are expressed only at a low level, some as low as a single copy per cell in some cell types. In certain cases it is advantageous to produce a library that has clones representing at the same level all the mRNAs in a cell or tissue, referred to as an expression-normalized library.

There are a variety of methods that have been used in an attempt to achieve library normalization Diatchenko et al., 1995, *Proc. Natl. Acad. Sci. U.S.A.* 93:6025–6030; Puzyrev et al., 1995, *Mol Biol* 29:97–103; and, Soares et al., 1994, *Proc. Natl. Acad. Sci. U.S.A.* 91:9228–9232. Most involve competitive or subtractive hybridization of the input MRNA used to make the library. The present invention provides means to transform a non-normalized library into a normalized one. The FACS/bead method proposed here offers a largely independent method to achieve normalization of libraries, which potentially gives the investigator more control over the end result because subsets of clones that have different abundance can be amplified separately and then recombined.

In a specific embodiment of the invention, tagged cDNA inserts, bearing identifier sequence tags, e.g., the 24-mers, amplified from a library as described supra, see, Section VI.C., supra, are hybridized in solution to random-primed cDNA made from mRNA isolated from the cells of interest. The cDNA is labeled with a first label, for example a fluorophore. After some appropriate time of hybridization under conditions that promote the formation of perfectly matched duplexes between the cDNA inserts derived from the library and the labeled cellular cDNA, the mixture is added to beads which have attached thereto capture oligonucleotides containing the complements of the oligonucleotides identifier tags, in the presence of free oligonucleotide identifier tag sequences comprising a second label as competitors. The second stage hybridization, under conditions that promote the formation of perfectly matched duplexes, is permitted to go to a high Cot (up to 24 hours). During this hybridization phase, the free oligonucleotide identifier tag sequences comprising the second label compete with the cDNA inserts, which are indirectly labeled with the first label through the cellular cDNA used during the first hybridization, for hybridization to the appropriate capture oligonucleotides attached to beads. The ratio of first and second label reflects the abundance of particular mRNA sequences in the original cells. The label attached to the competing free oligonucleotide identifier tag sequences provides a means to control the amount of capture oligonucleotide on the bead, i.e., it permits a comparison to be made, instead of an absolute measurement of fluorescence. For example, an abundant transcript such as actin will be identified by a large first/second label ratio on a bead that contains an actin cDNA clone attached via its identifier tag. A weakly expressed sequence is identified by a small first/second label ratio. If fluorescent labels are used, e.g., HEX and FAM, the population of hybridized beads are sorted on the FACS for prescribed first/second label ratios into particular bins, each bin representing cDNA clones derived from transcripts with a particular level of abundance. cDNA clones from particular bins are amplified to a particular level. After amplification, the cDNAs from each bin are re-mixed. This process results in heightened representation of weakly expressed sequences, and suppressed representation of abundant mRNAs. Altogether, the process produces normalization.

In another embodiment of the invention, a similar normalization procedure is carried out with cDNA clones representing the 3' ends of cellular transcripts. This results in a set of 3'ESTs, representing, theoretically, all transcribed genes in a particular cell or tissue. These EST tags may be used in subsequent experiments to monitor gene expression levels. For example, if clones prepared from the normalized 3'EST library are gridded out into 96-well trays and amplified individually by PCR, 10,000 such PCR reactions on 10,000 independent clones would produce a set that represents a large fraction of all 3' ends in the cell. If these are attached to beads, the beads may be pooled and used in hybridization experiments and, e.g., FACS analysis is used to determine expression profiles of genes in particular cells or tissues.

The collection of 3'ESTs generated in this fashion can also serve as a substrate for DNA sequencing directly, permitting EST comparisons to be made between cell types or tissues with the minimum sequencing redundancy.

G. Determination Of Relative MRNA Levels In Cells

Transcript levels in a cell are a meaningful indication of gene activity, in establishing a "molecular phenotype" of the cell. Mutations of certain genes may alter the expression pattern of other genes, and thus the molecular and possibly the physiological phenotype of the cell, which may result in severe pathological conditions, such as cancer. Therefore, information about relative transcript levels of specific genes in a cell is very valuable. However, measurement of transcript levels, though straightforward in the case of a few genes at a time, is, with currently available methods, a challenging task for large numbers of genes.

In some instances it may be even more valuable to obtain comparative expression information from genes in two or more different cell types, not simply relative expression levels within one cell type. For instance, when two cell types, e.g., a tumor cell and a normal cell, are compared, it is less interesting to focus on genes whose expression is unaltered, but of great potential significance to define genes whose expression is altered between the two cell types. The present invention provides a convenient mechanism for achieving this goal.

In an embodiment of the invention, comparison of the mRNA levels in different cell types, e.g., a tumor and non-tumor cell is accomplished essentially with the procedure described for library normalization, supra. However, instead of including a labeled free oligonucleotide identifier tag sequence for ratio comparisons, cDNA comprising a first label, derived from the tumor cell, is mixed with cDNA comprising a second label, derived from the normal cell, and hybridized during the first stage with identifier sequence-tagged cDNA library clones. The second phase of hybridization involves annealing of the tagged cDNAs, plus hybridized labeled cDNA, to the beads having attached thereto complements of the identifier tags as capture oligonucleotides. The beads are sorted, e.g., where fluorescent labels are used, by FACS analysis, to identify beads that have an unequal first/second label ratio. Such beads are collected, optionally re-sorted and/or rehybridized, and the attached cDNA insert sequences are amplified by PCR or cloned and then sequenced.

In another embodiment, comparative quantitation of mRNA levels in two cell types is achieved using beads having attached thereto random oligonucleotides as capture oligonucleotides, preferably of a length ranging from ten (10) to twenty (20) nucleotides. In most preferred embodiments, 15-mers are a useful compromise between the total complexity of the sample, i.e., $(4)^{15}=1.1\times10^9$, and the melting point (Tm) of the duplex that can be formed. Specifically, the complexity of 15-mers is very high, i.e., roughly one billion $(1.1\times10^9)$ different 15-mers, while the melting point of about 45° C. (depending on the base composition) allows hybridization at reasonably stringent conditions. If a target mixture of nucleic acids composed of similar or less complexity is exposed to beads that contain random 15-mers, each bead on average should hybridize to at least one target species. Given that an average mammalian cell contains roughly 10,000 active genes, each with about 2,000 nucleotides of unique sequence, the complexity of this population is about 20 million bp. If a random subset of the billion fold complex beads numbering two million is chosen, every target sequence of average length 500 bp should hybridize to one among the two million beads. Each 15-mer is expected, under certain conditions, to preferentially hybridize to specific sequences that are present in a complex target nucleic acid mixture. cDNA is prepared from the two sources to be compared, one cDNA sample is labeled with a first label, e.g., HEX, the other is labeled with a second label, e.g., FAM. The two cDNA populations are pooled and subjected to hybridization with beads having attached thereto the random capture oligonucleotides, e.g., random 15-mers. After hybridization to high Cot, the beads are washed and passed though a FACS sorter. Specifically, the beads are sorted based on HEX<FAM and FAM<HEX. All comparisons are internal, involving only fluorescence intensity ratios, not absolute intensities. If the labeled cDNAs have been prepared such that they contain PCR primer sites on both ends, the beads can be retrieved and the bound cDNA can be amplified, (possibly cloned) and sequenced.

H. Post-Passage Library Comparison

In a preferred embodiment, the methods of the invention are used to compare genetic libraries that have been grown in different host cells. Similar to the type of comparative analysis described in Section VI.F., supra, the methods can be employed to determine, for example, the effects of a particular mutation or alteration in a cell, or of agents that cause such a phenotypic change. Provided that the agent (termed "perturbagen") can be encoded by DNA, the bead hybridization technology allows isolation of the relevant causative agent. See, Internation Patent Publication WO 98/07886, published Fed. 26, 1998, incorporated hereby by reference in its entirety.

More specifically, a gene library, constructed in a vector that allows expression in the host cell types of interest, is introduced into one or more cell types. The host cells are permitted to grow for several divisions. Subsequently, the gene library is re-isolated using one of several possible procedures including PCR, see, supra, and biochemical enrichment is performed. This enrichment allows sequences that have been lost from one of the propagated libraries to be selectively amplified compared with sequences shared in common. Multiple rounds of library propagation, isolation, and biochemical enrichment may be required to achieve purification of the relevant differences in the library. This approach provides the means to identify specific sequences that are selectively lost from a library during propagation on particular host cells. Such differences are candidates for genes, gene fragments, or random sequences, depending on the library type, that cause arrest or cell death in a particular host cell or selective growth enhancement. Comparing sequences, referred to as "post-passage library comparison", permits those sequences that cause selective cell death or stasis in one cell type and not another to be recovered.

Choice of library and library size are important factors. If endogenous gene or gene fragment sequences are preferred, the libraries must be constructed from genomic DNA or cDNA prepared from the prospective host cell itself. If random sequences are desired, libraries need to be constructed that contain such inserts. It must contain enough independent clones to ensure that the relevant sequences will be contained in it. The library must propagate efficiently on, or be able to establish itself inside, the chosen host cells.

The characteristics of the cells used to propagate the library are also important, since sequences will be recovered from the procedure that affect the particular host cells and perhaps not others. This trait may be used to advantage so that library comparisons are made between the same library grown on different host cells. This permits recovery of library sequences that are, e.g., selectively lost from one host and not the other.

The problem of genetic drift also has to be considered. As libraries are propagated, random fluctuations in sequence representation will occur, a phenomenon akin to genetic drift in isolated populations of interbreeding organisms. Such random differences will introduce a type of noise into the process that may limit its effectiveness in isolating relevant sequences from the libraries that are lost during passage.

The degree of enrichment, i.e., the enrichment factor, during each step is an important variable. The extent of enrichment determines the number of cycles that must be performed before the sequences of interest can be recovered from the libraries. Enrichment occurs during two steps in each cycle; at the level of growth of the library on the host cells, and during the biochemical selection for differences that have appeared in the two libraries being compared.

The number of host cell doublings is also important. In certain cases, it may be desirable to limit the number of host cell doublings to avoid, for example, extensive genetic drift. In other cases, it may be helpful to prolong library propagation so that differences become accentuated.

Mutations occurring during the library propagation have also to be considered. Mutations may occur in library sequences either as they propagate in the host cells, or as they are isolated following propagation, particularly if PCR is used in this isolation process. Such mutations may limit the sensitivity of the comparison, because a mutant sequence that continues to propagate where the original sequence did not, may, if it remains similar enough in sequence to the original, confound or interfere with the biochemical enrichment steps.

The number of cycles is yet another important factor. The process of library propagation, re-isolation and biochemical selection could be repeated multiple times to achieve sufficient enrichment. This is a variable that needs to be determined based on other factors such as genetic drift, degree of enrichment per step, and mutation rates.

Gene Libraries.

Gene libraries, usually cDNA or genomic, can be constructed in a variety of vectors including plasmid and viral vectors by methods well-established in the art. See, among other references, Sambrook et al., supra. The library vectors can be designed to propagate on one or more of a variety of cell types including bacteria, yeast, or mammalian cells. In some cases the libraries are intended to be as representative of the nucleic acids present in a particular organism or tissue as possible. These are termed total genomic or cDNA libraries. In other cases the libraries are intended to contain only a subset of sequences; for example, those sequences that are prevalent in one cell type and absent in another. Such limited libraries can be constructed using, for example, cDNA from one source that has been treated with subtraction or blocking procedures as suggested above to remove sequences held in common with a second source. See, supra.

Libraries have traditionally been used in two ways; for biochemical screens and for genetic screens. The process of screening allows isolation of sequences of interest from the bulk of library sequences. Biochemical screens require a probe, either a nucleic acid probe or a protein probe such as an antibody (in the case of expression libraries). Specific genes or gene fragments can be fished out of a library using an appropriate probe. Genetic screens permit recovery of sequences from a library of genes or gene fragments which complement or rescue a particular mutant phenotype using an appropriate selection scheme. For example, if a yeast genomic library is introduced into HIS3-yeast cells and plated on media lacking histidine, only cells that have acquired library sequences that contain a functional HIS3 gene will be able to grow. These growing colonies can be treated such that the resident library sequences are recovered.

A number of ways can be envisioned to enrich and identify differentially expressed library members. For example, Representational Difference Analysis (RDA) permits the purification of sequences that differ substantially between two samples because, e.g., they contain a restriction fragment length polymorphism. RDA and similar methods are currently being used by commercial and academic research groups to identify resident pathogenic genomes and interesting lesions in tumors. For example, RDA was used to identify a homozygous deletion in a pancreatic xenograft which proved to include the breast cancer susceptibility gene BRCA2. Schutte et al., 1995, *Cancer Res.* 55:4570–4574. However, the resolution of RDA is rather limited; in addition, the method is not exhaustive, as it is subject to the inherent biases of PCR, including the tendency of certain fragments to dominate the amplification process.

A second approach is to use selective PCR amplification of sequences that are not held in common between two clones isolated from the same library, for example as described by Clontech, Inc., Palo Alto, Calif. Alternatively, biochemical enrichments may be used that involve solution hybridization followed by selective physical separation of hybridized sequences using, for example, biotinylated DNA and avidin beads.

The most sensitive and efficient way to compare the post-passage libraries is provided by the methods of the present invention. For example, if a library of cDNA fragments (tagged with identifier sequences) is introduced into two cell types and the cells are allowed to grow for several divisions, the library can be reisolated from each cell type and the individual clones from each library can be compared using the beads. PCR amplification of the sequences carried by the two cell types allows amplification of the individual clones, and labeling with, e.g., HEX and FAM separately such that one post-passage library carries HEX and the other carries FAM. If these passaged libraries are hybridized to beads and analyzed by FACS, cDNAs can be recovered that are over-represented or under-represented in one or the other cell type. For example, a specific cDNA clone that is over-represented in one cell type compared with the other cell types is a candidate for a sequence that selectively causes the first cell type to grow. The cDNA is also a candidate for a sequence that causes selective death or growth arrest in the second cell type. These interesting candidates can be studied further after their identification.

I. Data Management

As with any high throughput method capable of collecting a large body of information rapidly, data management is an important issue. With the invention described herein, the major types of information will be related to expression profile, DNA sequence, fluorescence intensity, and indirectly, effect of the sequences on cell growth. The data obtained may be conveniently handled using standard relational or spreadsheet data formats. In addition, in many cases it will be useful to search with each newly obtained sequence against local databases, i.e., against sequences identified through non-public experiments, and against global databases, e.g., databases derived from the efforts of sequencing the human genome. Sequence matches will allow extension of sequences obtained using the present invention, as well as, in some cases, correlation of an unknown sequence with a known gene. The "intensity" information can be used as a substitute for expression level or relative abundance of a particular nucleic acid sequence in a library.

Specialized tools can be envisioned to visualize the data that are obtained from the present methods in order to interpret the patterns of gene expression and the spectrum of biological effects that particular sequences exert in specific cell types. For example, such tools may involve multiple pairwise comparisons, or an averaging or summation method that depicts the cumulative results of several experiments in order to identify those nucleic acid sequences that are either most frequently altered in expression, or exert the most frequent or largest effect on cell growth. Many databases, sequence analysis packages, searching engines, and graphical interfaces are available either commercially or free over the internet. These include the Genetic Data Environment (GDE), ACEdb, and GCG. In many cases, off the shelf solutions to specific problems are available. Alternatively, software packages such as GDE readily permit customization to solve particular problems in sequence analysis, data storage, or data presentation.

J. Quantitation Of Genomic DNA Fragment Ploidy

In certain situations, it is useful to determine the ploidy, i.e., the copy number, of specific chromosomal regions or loci. For example, cancer cell regions that contain heterozygous deletions (LOH) or homozygous deletions often include tumor suppressor genes that are involved in the negative regulation of cell growth. In contrast, regions that contain DNA amplifications or translocations frequently contain oncogenes, i.e., genes that promote cell growth. Thus, the boundaries of aneuploid chromosomal regions can be used to localize genes that are involved in tumor progression.

Several methods have been used previously to localize regions of aneuploidy. These include cytogenetics Rowley, 1990, *Cancer Res.* 50:3816–3825, fluorescence in situ hybridization (FISH) van Dekken et al., 1990, *Cancer* 66:491–497, Comparative Genome Hybridization (CGH) Kallioniemi et al., 1992, *Science* 258:818–821, genotypic analysis using Restriction Fragment Length Polymorphisms (RFLPs) Botstein et al., 1980, *Am. J. Hum. Genet.* 32:314–331, Variable-length Nucleotide Tandem Repeats (VNTRs) Boerwinkle et al., 1989, *Proc. Natl. Acad. Sci. U.S.A.* 86:212–216, or microsatellite repeats Weber, 1990, *Curr Opin Biotechnol* 1:166–171, and RDA Lisitsyn et al., 1995, *Methods Enzymol* 254:291–304.

Cytogenetics, FISH, and CGH all utilize whole chromosomes mounted on solid supports such as glass slides. The combination of visible dyes or fluorescent dyes with microscopy permits identification of regions that contain gross chromosomal abnormalities such as LOH and amplification. In the case of CGH, much of the analysis has been automated. The weakness of these approaches primarily involves the level of resolution. Only lesions that are of considerable size, typically at least 10 megabases, can be detected with, e.g., CGH. Thus, smaller lesions, i.e., the vast majority of, e.g., homozygous deletions, are not detectable.

Genotyping via RFLPs, VNTRs, or microsatellites involves a comparison between tumor DNA and normal DNA from the same individual of polymorphic markers located at specific sites within the genome. If the relative intensities of two alleles at a particular marker locus differ significantly between the tumor and normal sample, the locus is considered to be aneuploid. If cell lines are used, such comparisons are often not possible. However, homozygous deletions can be detected easily by the failure of particular sequences within the deletion to amplify. These methods suffer from the drawback that a great deal of labor is required to achieve high resolution. For example, if a genome wide search for aneuploidy is undertaken at a ten (10) megabase resolution, a minimum of 300–500 markers is required.

RDA is a PCR-based approach that has been used to detect RFLPs, some of which prove to be sites of aneuploidy in a tumor sample. The approach has been especially effective in isolation of fragments derived from homozygously deleted regions Schutte et al., 1995, *Cancer Res.* 55:4570–4574. The approach involves hybridization between restriction enzyme-digested, PCR-amplified "driver" tumor DNA and "tracer" normal DNA. Sequences shared between the two samples are removed as potential PCR templates by formation of hybrids between tumor and normal DNAs. These hybrids are treated so that they fail to amplify in a subsequent PCR step. Only sequences from the tracer sample that are not shared with the driver DNA can be amplified. After multiple rounds of hybridization and PCR, such unique fragments emerge as individual products that can be visualized on gels and cloned. The weakness of RDA is that of necessity it involves a step to reduce complexity of the total genomic DNA mixture, i.e., the first PCR step, thus limiting the resolution of the process. In addition, the method is technically demanding and subject to the inherent biases of PCR, including the tendency of certain fragments to dominate the amplification process.

The present invention provides a solution to many of the inherent weaknesses of the currently available strategies for isolation of aneuploid chromosomal regions. Specifically, the beads having attached thereto capture oligonucleotides or nucleic acid fragments are used to bind individual genomic DNA sequences, labeled to permit quantitative comparisons of DNA content between two samples. Several specific procedures to accomplish this task can be envisaged. One approach involves generation of a germline genomic DNA library by shearing genomic DNA to an average size of about 500 bp. These fragments are attached to linkers that contain identifier tags, and inserted into an appropriate phage or plasmid cloning vector. For a human genome-sized library, for example, a total of about 6 million clones are required. An equivalent number of beads with cognate identifier sequence tag complement oligonucleotides are also needed. Hybridization of the beads to the genomic library permits the individual clones to be spread out one by one over the set of beads. These genomic fragments can then be hybridized in a second round to a mixture of two genomic DNA samples each labeled with a different fluorescent dye (the order of these two hybridization reactions could be inverted). FACS analysis permits recovery of beads that have bound a ratio of dye molecules that deviate significantly from unity. The fragments of library genomic DNA, i.e., library inserts originally prepared so that they have PCR primer sites, for analysis, bound to the beads can be eluted from the beads and amplified by PCR. These fragments can be aligned to the human physical map either based on their DNA sequence or by additional PCR experiments. Thus, the positions of LOH regions, homozygous deletions, and amplifications can be defined.

K. Comparison Of Promotor Activity

An alternative method for assessing gene activity encompassed in this invention involves the assessment of promoter activity in specific cell types. Specifically, genomic library fragments are identified which drive expression of a reporter gene in certain cellular environments. Such an approach permits an indirect functional analysis of the transcriptional factor milieus of different cells. This strategy is based on the fact that genes can be activated by promoter fusions, i.e., insertions, typically upstream, of transcriptional activation sequences that induce transcription of adjacent genes.

In the specific formulation of the strategy relevant to the invention described herein, a genomic library with inserts ranging from a few basepairs to several kilobasepairs is inserted into a vector such that each of the derived clones in the library has a sequence identifier tag attached. The size of the library can vary, but most typically will not exceed ten (10) million independent clones. The identifier tags are located between a poly(A) addition site and a reporter sequence that produces a stable transcript. The library is introduced independently into two cell populations. These cell populations may represent different cell types, or may be derived from the same cell type, where one population has been treated differently, e.g., with a small molecule compound under study. The cells are allowed enough time to express the introduced library sequences prior to harvesting and conversion of cellular RNA into labeled cDNA. In general, only genomic DNA sequences capable of inducing RNA expression of the reporter sequences, i.e., promoters, will produce significant amounts of transcript that can be detected subsequently by hybridization to beads. Because the cDNAs from the two samples are labeled with different dyes, the ratio of signal intensities emitted by the two dyes can be used to identify genomic sequences that are differentially active in the two cell populations. These differences may reflect disparities in the active transcriptional machinery in particular cell populations. Such differences may be useful in assessing, for example, the degree to which a particular stimulus or agent affects a particular cell type, especially in a differential manner compared to another cell type. Such differences may be indicative of potential side effects that a drug candidate may produce. The technique may also allow recovery of promotor sequences that have differential activity in two cell types or tissues, an achievement that has relevance in gene therapy, e.g., for the targeting of gene activity in specific cell types.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

EXAMPLES

A. Example 1

Synthesis of Capture Oligonucleotides on Beads Using Base-Stable Chemical Linker This example illustrates the chemical synthesis of capture oligonucleotides on the surface of beads such that the resulting capture oligonucleotides were covalently joined to the bead surface via their 3' ends and do not dissociate from the bead in the presence of base concentrations sufficient to remove deprotecting groups from the bases.

Polystyrene beads of diameter 30 microns in diameter derivatized with primary amines were obtained from Pharmacia and exposed to standard coupling chemistries in an ABI 394 DNA synthesizer (Applied Biosystems, Foster City, Calif.). The initial coupling step involved the attachment of a phophoramidite base to the bead via nucleophilic attack of the primary amine. This linkage was oxidized to a phosophoramidate by treatment with molecular iodine. The phosphoramidate linkage was base stable and the beads were now treated in the same manner as resins used during standard oligonucleotide synthesis in terms of reagents and cycle times. The extension products were stable and the beads can be used for hybridization as illustrated in subsequent examples.

B. Example 2
Sorting Of Beads Using A Fluorescence-Activated Cell Sorter

This example illustrates the sorting of nucleic acids captured by beads with a fluorescence activated cell sorter (FACS).

Nucleic acid pools derived from two different sources are labeled with two different fluorophores, one with HEX, the other one with FAM. The beads with covalently attached capture oligonucleotides are hybridized using stringent conditions to equal amounts of nucleic acids derived from the two different sources. More specifically, 100,000 beads containing on their surfaces roughly 10–100 million copies per bead of a random 15-mer sequence are placed in 100 $\mu$l of hybridization buffer (2×SSPE, 0.1% Triton) along with equal amounts of FAM-labeled cDNA and HEX-labeled cDNA from different sources, and heated to 95° C. in a thermocycler (MJ Research) for 2 minutes. The mixture is cooled to 40° C. and left to hybridize for 24 hrs. The sample is then washed three times at room temperature in 1×SSPE, 0.1% Triton, followed by resuspension in 1 ml of PBS. The hybridization reaction can be scaled up to include more beads, e.g., 2–5 million. Subsequently, the beads are sorted using a FACS machine in order to identify those which are labeled with an excess of HEX or an excess of FAM. FIG. 1 shows the capture oligonucleotides attached to the bead surface as black squiggly lines. The gray (F) and black (H) lines represent chromophore-labeled cDNAs from two different sources.

Figure 2:
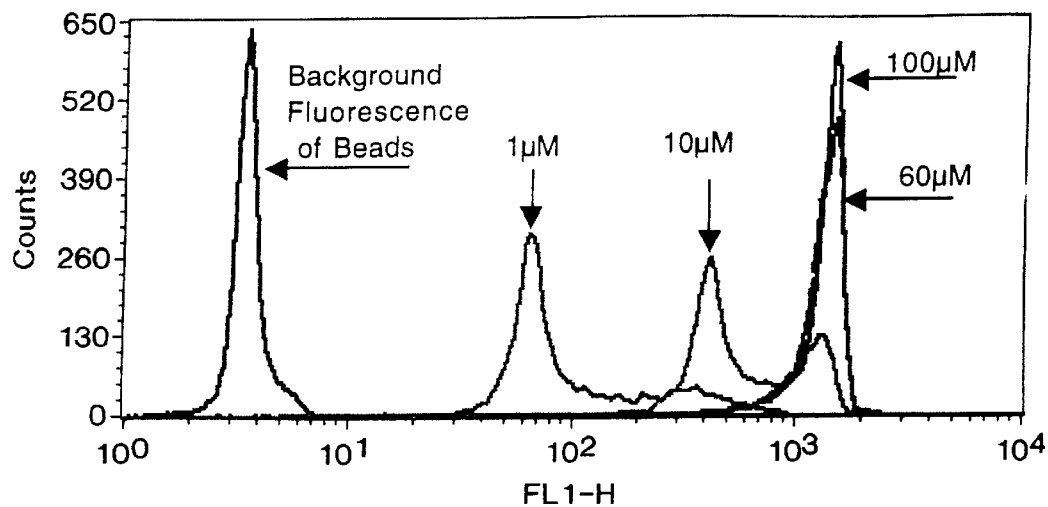
FIG. 2 depicts the sensitivity of the oligonucleotide-conjugated beads in hybridization and FACS analysis, as described in Example 3, infra.

C. Example 3
Sensitivity Of The Oligonucleotide-Conjugated Beads: Signal/Noise Ratio The following experiment shows the sensitivity of the oligonucleotide-conjugated beads in hybridizations and FACS analysis. As depicted in FIG. 2, the signal/noise ratio was as low as 1000:1, calculated by dividing the saturating fluorescence at 60 $\mu$M by the background autofluorescence.

50,000 beads were used having attached to their surface an estimated 1–10×10$^8$ copies of capture oligonucleotide CO1 (SEQ ID NO:1) per bead. The hybridization conditions were as follows: The 50,000 beads in 100 $\mu$l of 2×SSPE, 0.1% Triton were mixed with the complement of CO1 (CCO1), which was labeled with FAM at the indicated concentrations (FIG. 2) and the sample was heated to 95° C. for 3 minutes, followed by annealing at to 55° C. for 15 minutes. The beads were then pelleted and washed 3 times in 70° C. 1×SSPE, 0.1% Triton to remove the unbound labeled CCO1. Finally, the sample was resuspended in PBS and analyzed on the Becton Dickenson FACScan Flow cytometer (Becton Dickenson, San Jose, Calif.).

FIG. 2 shows a histogram of the number of events, i.e., beads, plotted against the fluorescence intensity. The labeled peaks represent beads that have been hybridized overnight with the chromophore (FAM)-labeled complementary oligonucleotide at different concentrations ranging from zero (0) (background) to 100 $\mu$M.

Figure 3:
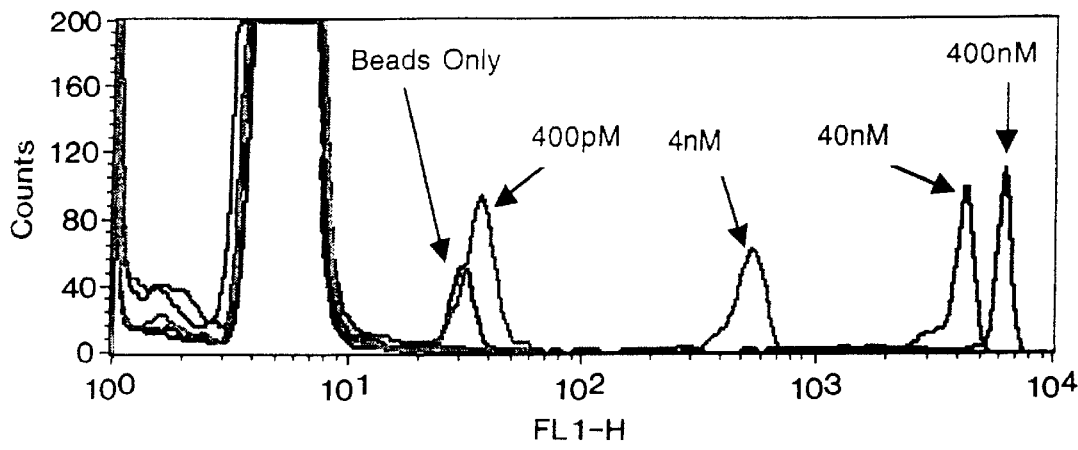
FIG. 3 depicts a representation of results of a FACS analysis showing sensitivity of the oligonucleotide-conjugated beads when 1% of the beads hybridize to the target and 99% do not, as described in Example 4, infra.

D. Example 4
Sensitivity Of The Oligonucleotide-Conjugated Beads: Range Of Sensitivity The following experiment shows that 1% specific beads can be distinguished from the 99% nonspecific, unhybridized beads by a FACS instrument. As depicted in FIG. 3, the sensitivity of the technique is sufficiently high that a target concentration of between 400 pM and 4 nM can easily be detected above the background ("beads only").

In this experiment, two populations of oligo-conjugated beads were mixed prior to hybridization. One population contained the specific oligonucleotide, while the second population, present at a 100-fold higher concentration, contained a different, unrelated oligonucleotide. Capture oligoucleotide 1 (CO1) was directly synthesized on 1% of the beads and CO2 on 99% of the beads. Both CO1 and CO2 were 20 base oligonucleotides. The sequence of CO1 was: GCT GCA TAA ACC GAC TAC AC [SEQ ID NO: 1], and is derived from the *E. coli* LacZ gene sequence. The sequence of CO2 was also derived from LacZ: GCA TTA TCC GAA CCA TCC GC [SEQ ID NO:2]. The beads were estimated to contain on average about 1×10$^9$ copies of each sequence on their surfaces. The conditions of hybridization were as follows: 100,000 total beads were incubated in the presence of the indicated concentration of complementary CCO1, labeled with FAM, in 2×SSPE, 0.1% Triton. The 100 $\mu$l reaction was heated to 95° C. for 3 minutes and then hybridized at 55° C. for 15 hours. The beads were pelleted by centrifugation and the supernatant containing the unbound fluorescent oligo was removed. The pelleted beads were washed three times with 500 $\mu$l of 70° C., 1×SSPE, 0.1% Triton. The beads were resuspended in 600 $\mu$l PBS before analysis on a Becton Dickenson FACScan flowcytometer (Becton Dickenson, San Jose, Calif.).

FIG. 3 shows a histogram of the number of events, i.e., beads, plotted against the fluorescence intensity. The labeled peaks represent beads that have been hybridized overnight with the chromophore (FAM)-labeled complementary oligonucleotide at different concentrations.

Figure 4:
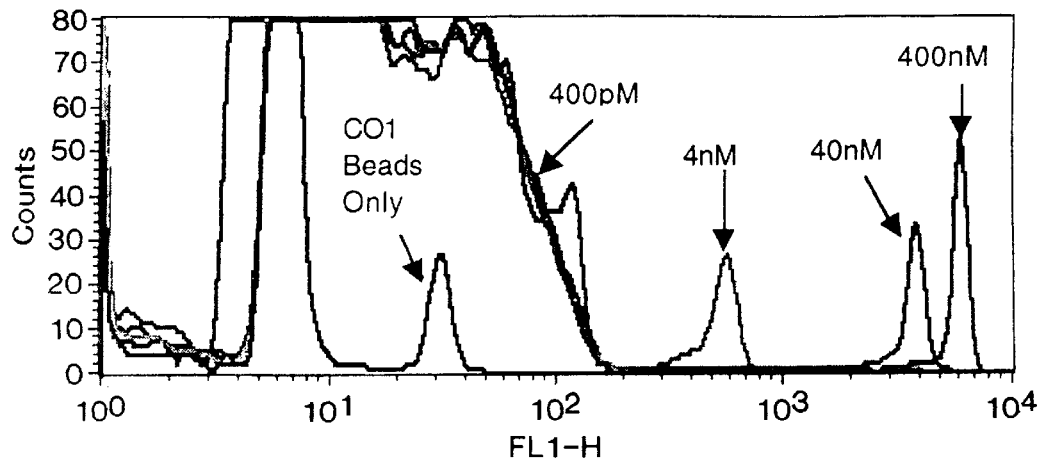
FIG. 4 depicts the signal/noise ratio in the presence of 10 micromolar nonspecific sequences, as described in Example 5, infra.
Figure 5A:
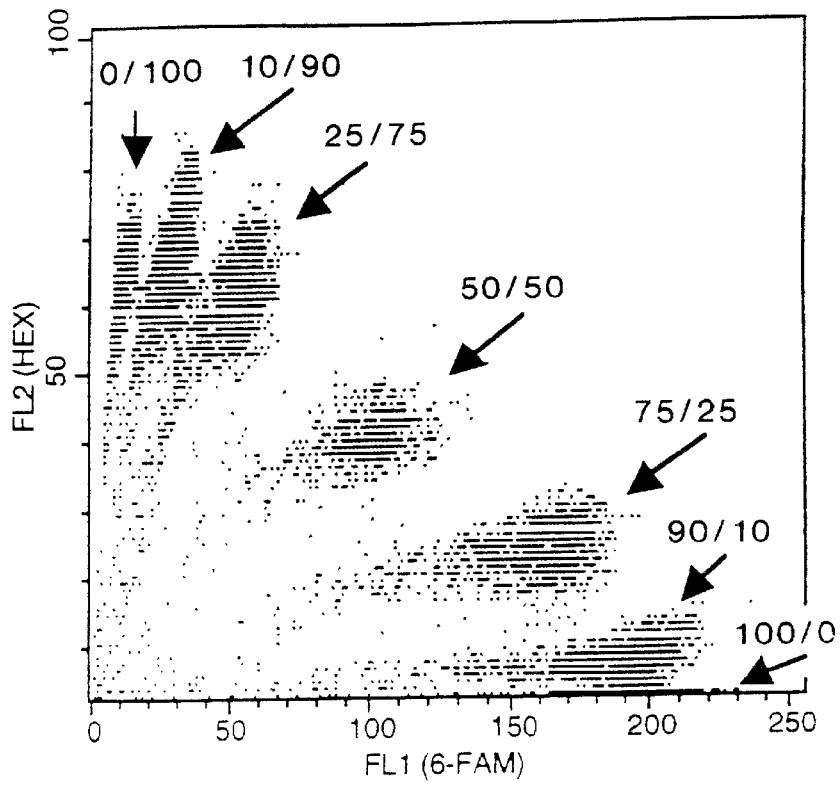
FIG. 5 depicts the sorting of labeled beads based on fluorescence intensity ratios, as described in Example 6, infra.
Figures 1, 5B:
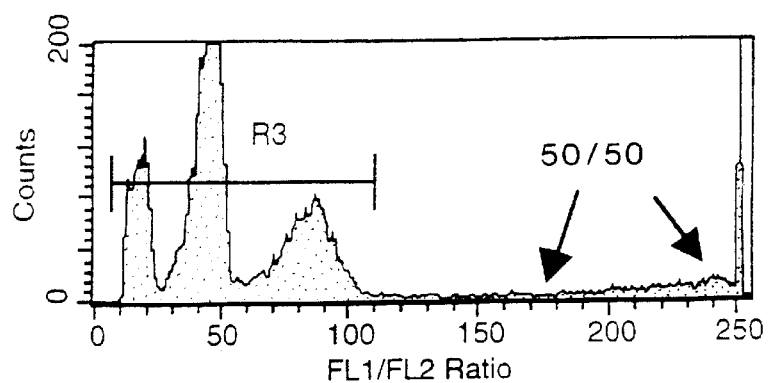
Figures 2, 5B:
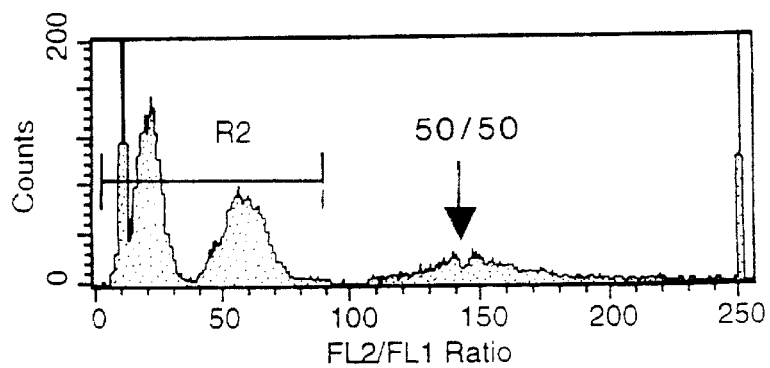
Figure 5C:
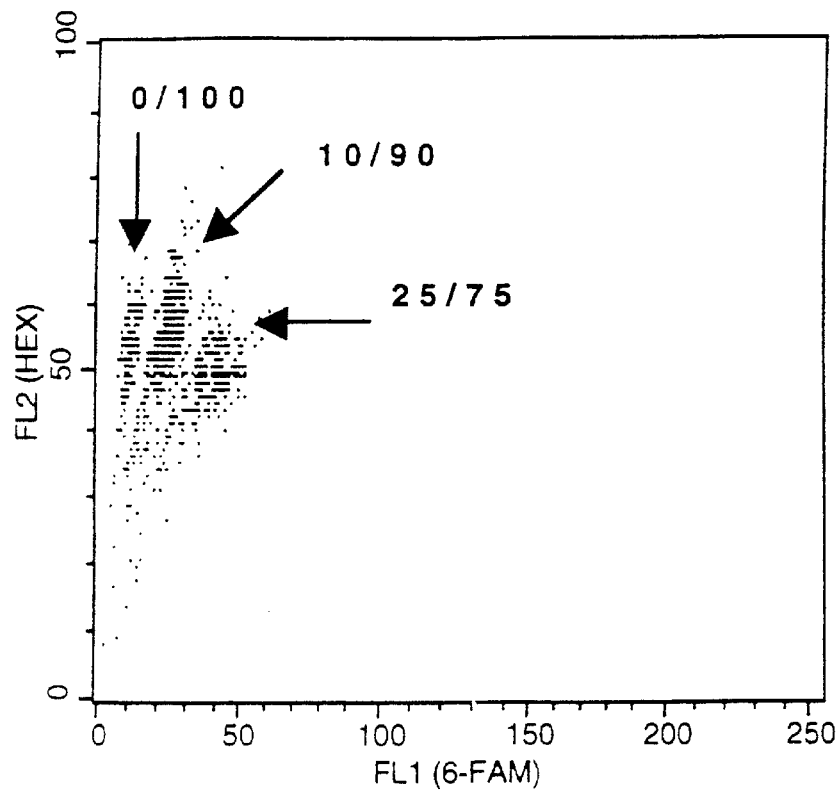
Figure 5D:
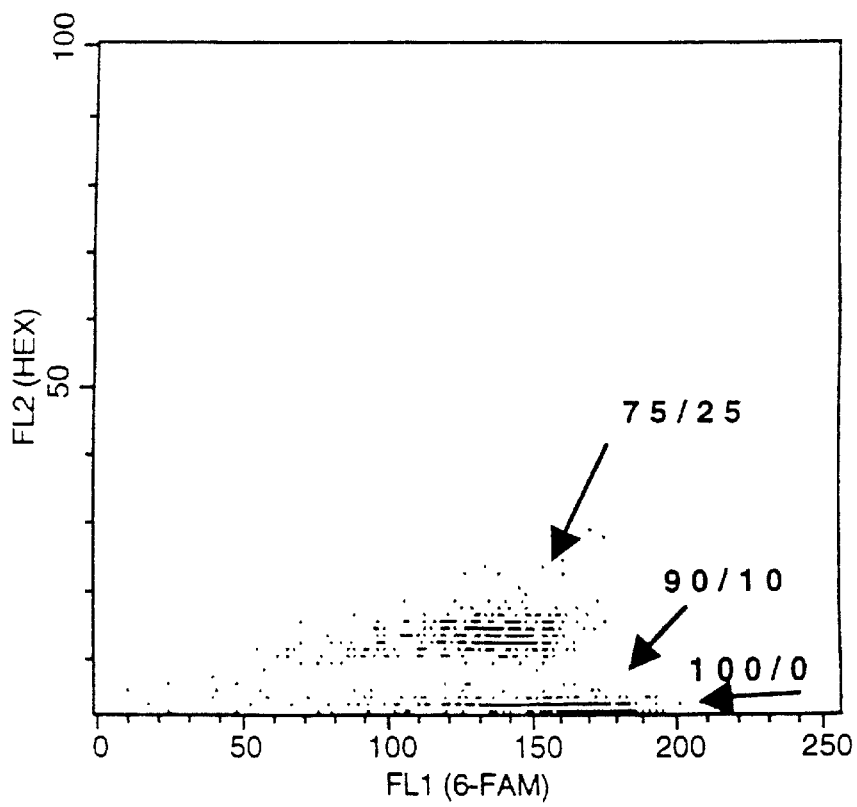

E. Example 5
Sensitivity Of The Oligonucleotide-Conjugated Beads: Determination Of Background Noise The following experiment is essentially the same as in Example 2, except that a high concentration (100 $\mu$M) of nonspecific target oligonucleotide, unrelated to the oligo sequence on the beads, was included in the hybridization. This permits an assessment of the background noise caused by nonspecific nucleic acids in the experiment. As depicted in FIG. 4, the signal/noise remains high even in the presence of a roughly 100,000-fold excess of nonspecific sequences.

F. Example 6
Sorting Beads Based on Fluorescence Intensity Ratios

The following example shows how fluorescence intensity ratios of two different fluorophore labels can be used to sort beads into distinct populations, each population having a defined intensity ratio.

A Becton-Dickenson "FACS Vantage" cell sorter was used with "Cell Quest" software and an argon laser (Becton Dickenson, San Jose, Calif.) to excite FAM and HEX dyes attached to oligonucleotides captured by beads conjugated with complementary oligonucleotides. Two filters were used: a 530+/−15 nm filter to detect FAM emission and a 585+/−21 nm filter to detect HEX emission. 40,000 beads conjugated with LacZ2RA' oligonucleotide (sequence CC GAG TGT GAT CAT CTG GTC [SEQ ID NO:3]; roughly 1–10×10⁹/bead) were exposed in a 50 µl volume of 2×SSPE, 0.1% Triton solution to oligonucleotides. Various ratios of HEX- or FAM-labeled LacZ2RA' oligonucleotide including FAM:HEX of 100:0, 90:10, 75:25, 50:50, 25:75, 10:90, 0:100. The combined concentrations of the labeled oligonucleotides was 4 µM in all samples. The reaction solution was heated first to 95° C. for one minute, and allowed to anneal at 30° C. for 10 minutes. Every 90 seconds the samples were vortexed. The beads were then washed 3× at room temperature in 1 ml of 1×SSPE, 0.1% Triton. The beads were then resuspended in 1 ml of PBS, 0.05% Triton at room temperature prior to FACS analysis.

Detectors on the FACS were optimized using the beads labeled with FAM:HEX 100:0 and 0:100, and the "ratio sorting gates" using beads labeled 50:50. After FACS optimization, the beads were mixed and passed through a 62 µm mesh to eliminate bead doublets that clog the 70 µm sorting tip. Approximately 10,000 beads in sort gates R2 and R3 were collected and then rerun on the scanner to demonstrate sorting efficiency.

Panel A of FIG. 5 shows the mixed population of beads shows that all seven bead subpopulations can be seen as distinct clusters. Panel B of FIG. 5 shows the FAM/HEX fluorescence ratio of the mixed population of beads and the R3 gate used to sort the beads of interest (see, Panel B1). This ratio provides resolution of the beads that have HEX<FAM. Panel B2 shows the R2 gate used to sort beads of interest and the HEX/FAM ratio provides resolution of beads where FAM<HEX. Panel C of FIG. 5 shows the beads that were sorted using R3 sort gate in Panel B1 were re-run on the sorter to demonstrate that only the beads of interest were collected. Panel D of FIG. 5 shows the beads that were sorted using the R2 sort gate in Panel B2 and were re-run on the sorter to demonstrate that only the beads of interest were collected.

G. Example 7
Pool And Split Synthesis Of Random Oligomers

The following example shows the pool and split synthesis strategy for the generation of random oligomers (N-mers).

Figure 6:
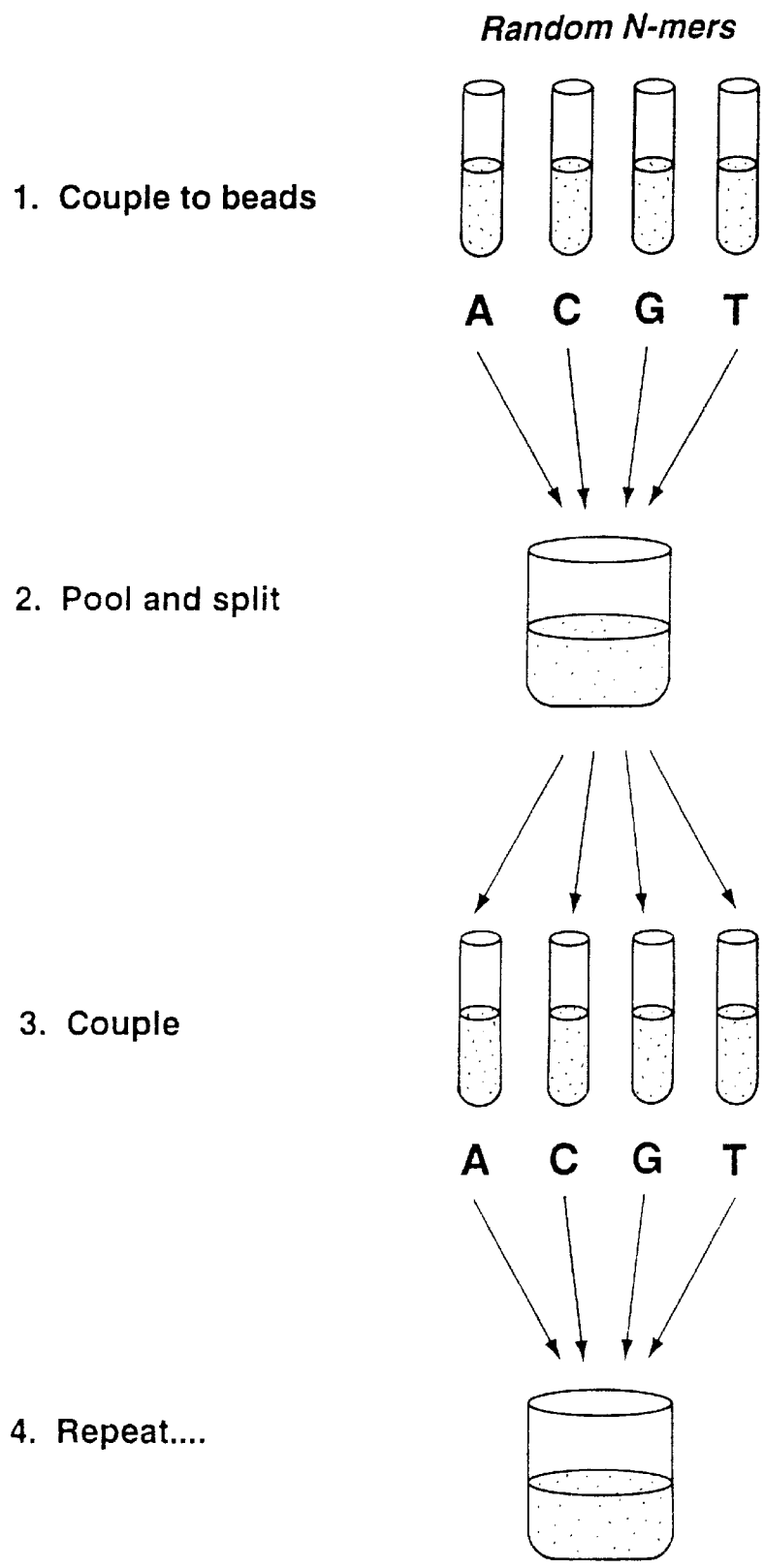
FIG. 6 depicts the concept of the "split and recombine" synthesis strategy for the generation of random N-mers wherein N is the length of the oligonucleotide, as described in Example 7, infra.

As depicted in FIG. 6, after an initial round of base couplings in four separate synthesis columns, the resins from each column are pooled and redistributed (split) equally into four new columns. The mixing process is completed after each new round of coupling to generate random N-mers, where N is the length of the oligonucleotide.

H. Example 8
Pool And Split Synthesis Of 24-mers

The following example illustrates the concept of the "pool and split" synthesis strategy for the synthesis of 24-mers comprising 3 unique 8-mers in tandem.

To synthesize 24-mers that are roughly one million-fold degenerate, a 96-well format is used. After 8 rounds of coupling, each well (or column) has obtained a unique 8-mer sequence; the contents of the 96 columns are pooled, mixed, and redistributed (split) into another 96 columns for a further 8 rounds of base coupling. The process is repeated again to generate the final 24-mers. See, FIG. 7. For clarity only one recipient well of each run and 8 donor wells are shown as being mixed.

I. Example 9
Synthesis Of Sequence Identifier Tags

The following example describes the synthesis of sequence identifier tags.

Two strategies are used to capture specific sequences from a complex mixture of nucleic acids. The first involves use of random (or a biased subset of random sequences), e.g., 15-mers attached to beads. In practice only about two million of the total one billion possible 15-mers need be used. These 15-mers will bind to sequences present in the target population of nucleic acid (usually cDNA) based on the likelihood that a given sequence contains a particular 15-mer complementary sequence within its bounds. The cDNA is typically generated by random priming MRNA, with an appropriate primer. The beads do not interact with the primers, but rather with unique sequences within the cDNA itself.

An alternative strategy involves hybridization of bead-conjugated oligonucleotides to cDNA complementary to the 3' ends of mRNAs. In this approach, the beads contain a stretch of A residues (e.g., 15 A's) followed by a stretch of random or pseudo-random sequence (e.g., 10 residues of random sequence). Target cDNA is prepared by oligo-(dT)-priming and is labeled with a fluorophore. When this cDNA is hybridized to the beads at high stringency the unique 3' cDNA sequence adjacent to the oligo-dT stretch finds its complement among the unique 10 basepair sequences adjacent to the oligo-dA stretch on the bead. Thus, the specificity is determined by the unique sequence, but the hybridization and washing temperatures can be relatively high, e.g., 60–70° C. In a preferred embodiment of the invention, oligonucleotides comprising a stretch of from about 5 to about 25 adenosine residues at the 3' end, and a stretch of from about 8 to about 16 nucleotides of random sequence at the 5' end are attached to solid supports such as beads.

Figure 8:
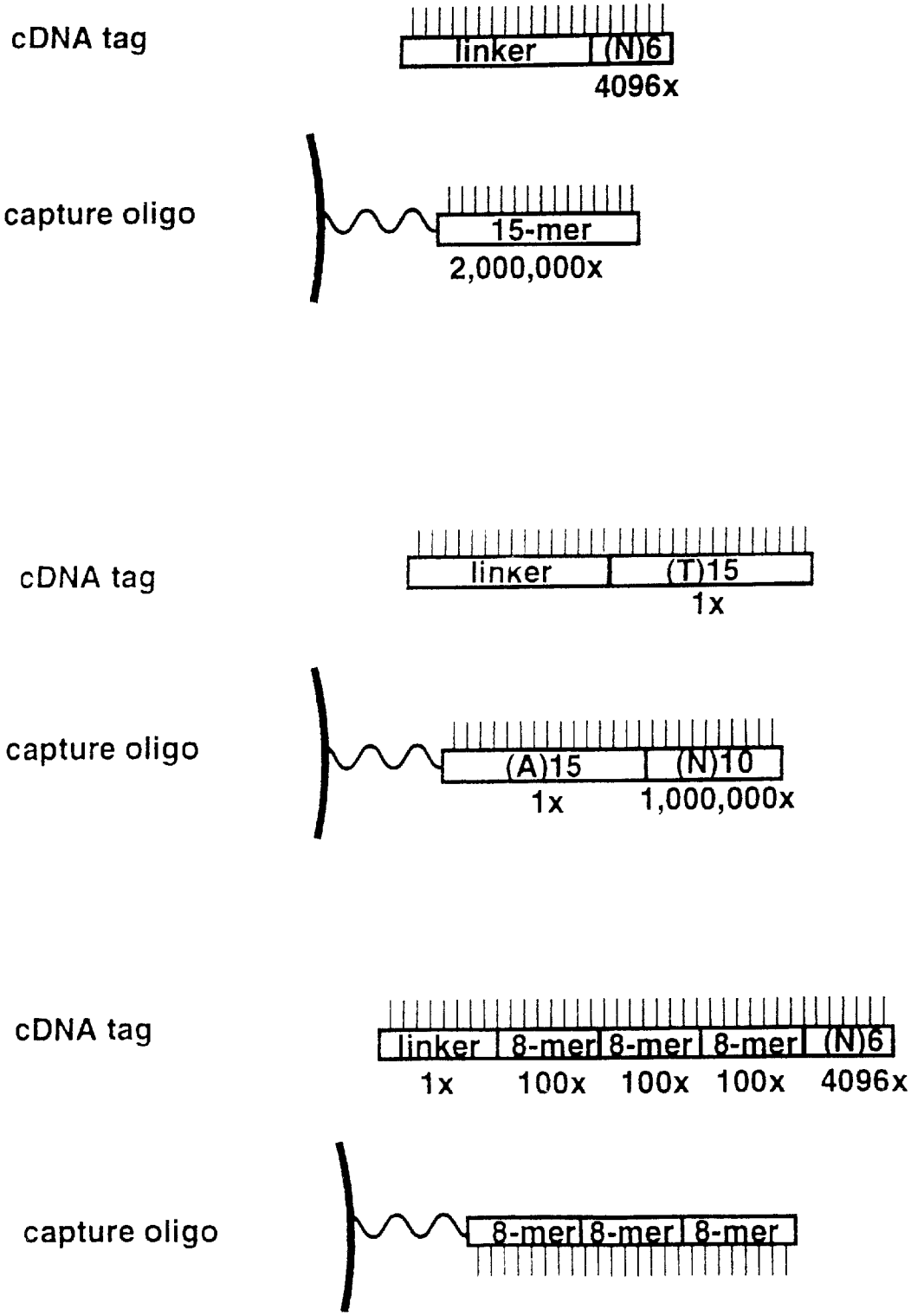
FIG. 8 depicts the use of sequence identifier tags. Three strategies to capture specific sequences from a complex mixture of nucleic acids using sequence identifier tags are illustrated. The first at the top of the drawing involves use of random (or pseudorandom), e.g., 15-mers attached to beads. The second strategy involves the capture of oligo (dT)-primed cDNA. The third strategy, depicted at the bottom half of the drawing, involves priming of the MRNA with a mixture of 24-mers, one million-fold degenerate in total. See, Example 9, infra.

A different strategy involves priming of the MRNA with a mixture of 24-mers (one million-fold degenerate in total). The primers also have a constant region (linker) at their 5' ends and a random N-mer (e.g., hexamer) at their 3' ends for random priming. cDNA clones generated by this method can be captured through the 24-mer sequences that they carry from the original priming event that produced them. FIG. 8 shows this use of sequence identifier tags.

The choice of primer sequences can be made based on a simple algorithm implemented on a computer. Random 8-mer sequences can be generated with a variety of constraints. For a given set of, e.g., 100 sequences, each 8-mer that is generated by computer can be examined for G/C content and secondary structure. Sequences that have unacceptable G/C content (e.g., this might be simply any sequence that is not 50% G/C), secondary structure potential (e.g., any sequence that has self complementarity of greater than 3 consecutive bases) can be rejected. Of the roughly 64,000 possible 8-mers, there are 17,920 that contain 50% G or C residues. Therefore, the computational problem is reduced to searching this set for those that are mutually compatible according to the criteria that they are minimally cross-hybridizing and have minimal secondary structure. This problem can be solved in a variety of ways known in the art. Most importantly, the sequences are chosen so that they differ maximally in primary sequence from one another; i.e., there are no stretches of identity that extend beyond 2–3 bases among the set of 100. Applying these constraints on the choice of 8-mers produces a set of 100 sequences predicted to be optimal as identifier tag components. Such constraints can be applied to each set of identifier tag units that is generated. In the end, the final, e.g., 24-mers, can be examined to ensure that each member of the final set has minimal self complementarity (or complementarity with other set members). Problem sequences can be identified and rejected at this point, and these sequences can be replaced by others generated in the initial 8-mer sets.

The synthesis can be performed on standard automated DNA synthesizers such as those sold by Applied Biosystems or Pharmacia. Because a relatively large number of parallel synthesis must be performed (e.g., 100), it is helpful to use synthesizers that have many columns. Alternatively, synthesizers with fewer channels can be employed in succession so that 100 different sequences are generated. These 100 columns are broken down and the resin contained within is collected and pooled. It is then split into 100 equal portions either by weighing out equal masses or by resuspending in a convenient volume of liquid (e.g., acetonitrile) and then pipetting equal volumes. One hundred new columns are then fabricated using the mixed contents of the previous set, and the synthesis is repeated. The pool and split process is completed as many times as necessary to generate the final combinatorial set of beads.

J. Example 10
Hybridization Discrimination Of Sequence Identifier Tags

The following example illustrates the hybridization discrimination of sequence identifier tags, as depicted in FIG. 9.

The 24-mers on the beads should bind with high specificity to their complements on the cloned cDNA. Other than a perfect match, the most similar hybrids that might ensue consist of complexes that have multiple mismatches in one, differing on average by roughly 24° C. in their melting point (Tm). Estimating Tm values for specific sequences is difficult and the calculation involves free energy difference calculations if it is to be performed rigorously. However, even when strict methods are employed the results can vary from experimental values. There are several computer programs that estimate Tm's for defined oligonucleotide sequences. Alternatively, a simple formula (Tm=4(number of G/C basepairs)+2(number of A/T basepairs)) gives a reasonably accurate indication of the Tm of a specific sequence. If the, e.g., 24-mers described infra are generated with 50% G/C content, then the predicted Tm of a particular 24-mer is expected to be 72° C. under typical hybridization conditions. This Tm depends on several factors—especially salt concentration—that can be manipulated to alter the Tm. Since 24-mers that are most similar to one another differ in one of their 8-mer units, this should cause a decrease in Tm of the mismatched identifier sequence of, e.g., 24° C.

K. Example 11
Synthesis Of cDNA Comprising Sequence Identifier Tags

The following example describes the generation of cDNA comprising sequence identifier tags.

Figure 10:
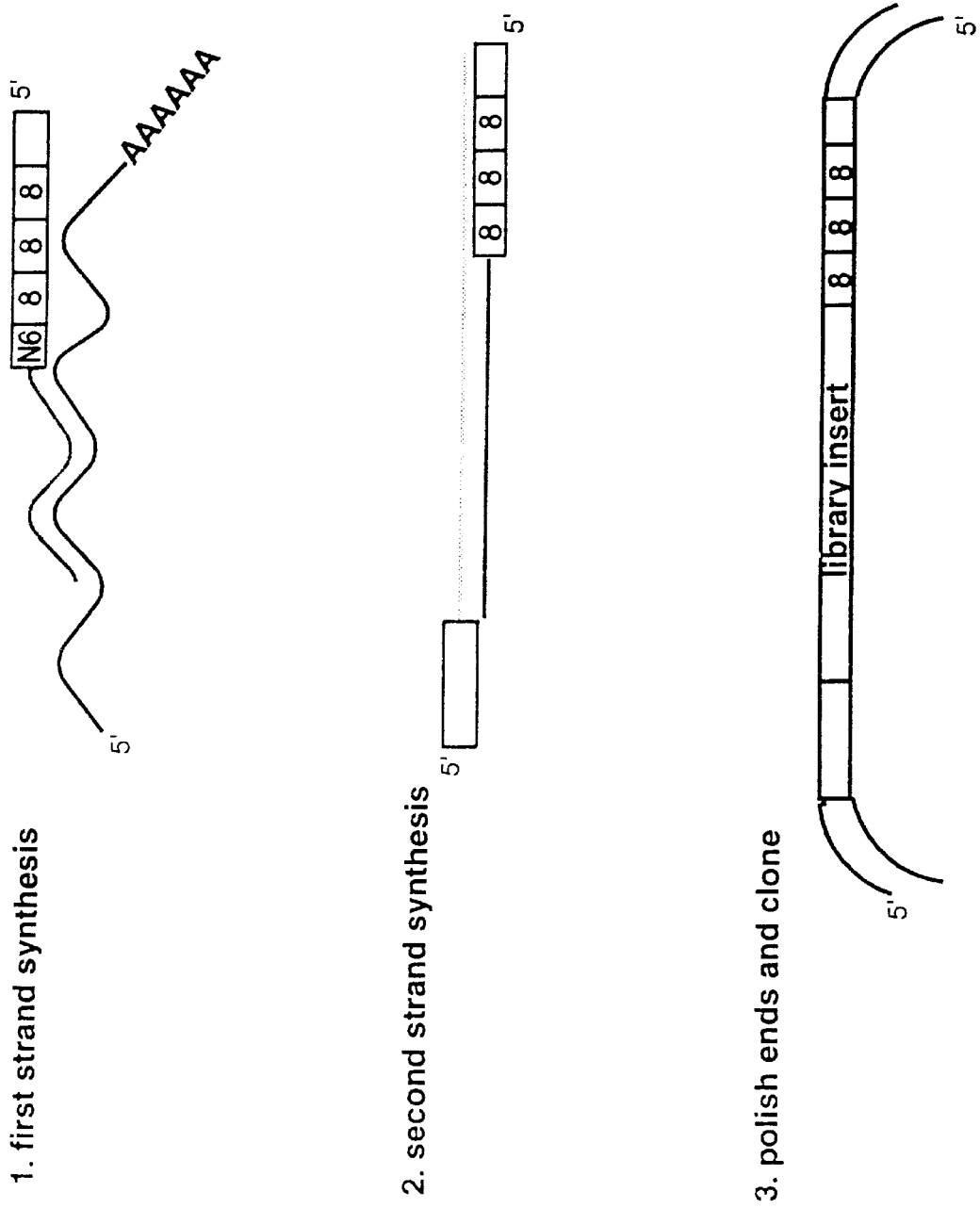
FIG. 10 depicts the generation of double stranded cDNA marked with identifier tags, as described in Example 11, infra.

A typical reaction to generate double-stranded cDNA marked with identifier tags involves first strand synthesis from a primer that contains the 24-mers and associated sequences. This first strand is converted into a second strand by one of several second strand synthesis procedures. The ends of these double-stranded cDNA fragments are repaired and inserted into an appropriate cloning vector for introduction in *E. coli*. See, FIG. 10. For first strand synthesis, the primers contain the degenerate population of, e.g., 24-mers discussed, infra. If the synthesis involves oligo(dT) priming, the 3' end of the primer includes a stretch of 8–16 T residues; if random-priming is desired, the 3' end includes a random sequence, e.g., a hexamer of random sequence. In certain cases, the 5' end of both random primer and oligo(dT) primers may include an additional linker sequence useful in cloning or in subsequent PCR experiments; e.g., a restriction endonuclease recognition sequence. Conditions for first strand synthesis are known in the art. For example, poly(A) selected RNA is denatured in 10 mM methylmercuric hydroxide at 65° C. for 5 minutes, followed by addition of 2-mercaptoethanol to 32 mM. Primer is added to a concentration of 30 uM, reverse transcriptase buffer (e.g., from BRL), 5 mM DTT, 400 $\mu$M dNTP's, 0.8 units/ul RNasin, and Superscript II reverse transcriptase at 200 units/mg of RNA. After one hour at 37° C., the enzyme is heat denatured at 65° C. and the first strand cDNA is purified by gel chromatography, e.g., on Sepharose CL-4B columns. Methods for second strand synthesis are also known in the art. One procedure involves treatment of first strand material in 25 mM Tris acetate pH 7.7, 50 mM KOAc, 10 mM Mg(OAc)$_2$, 10 mM(NH$_4$)$_2$SO$_4$, 5 mM DTT, 50 $\mu$M dNTP's, 150 $\mu$M NAD, 100 $\mu$g/ml BSA, and RNase H, *E.coli* ligase, DNA polymerase I at 1.6, 4.0, and 40 units/$\mu$g input cDNA, respectively. The reaction proceeds at 14° C. overnight, and double-stranded cDNA is purified on Qiaex beads (Qiagen, Chatsworth, Calif.). To polish the ends, double-stranded DNA is for 30 minutes treated at 15° C. with T4 DNA polymerase and T7 DNA polymerase at 3.3 and 6.7 units/$\mu$g input first strand cDNA, respectively.

L. Example 12
Enrichment And Recovery

Figure 11:
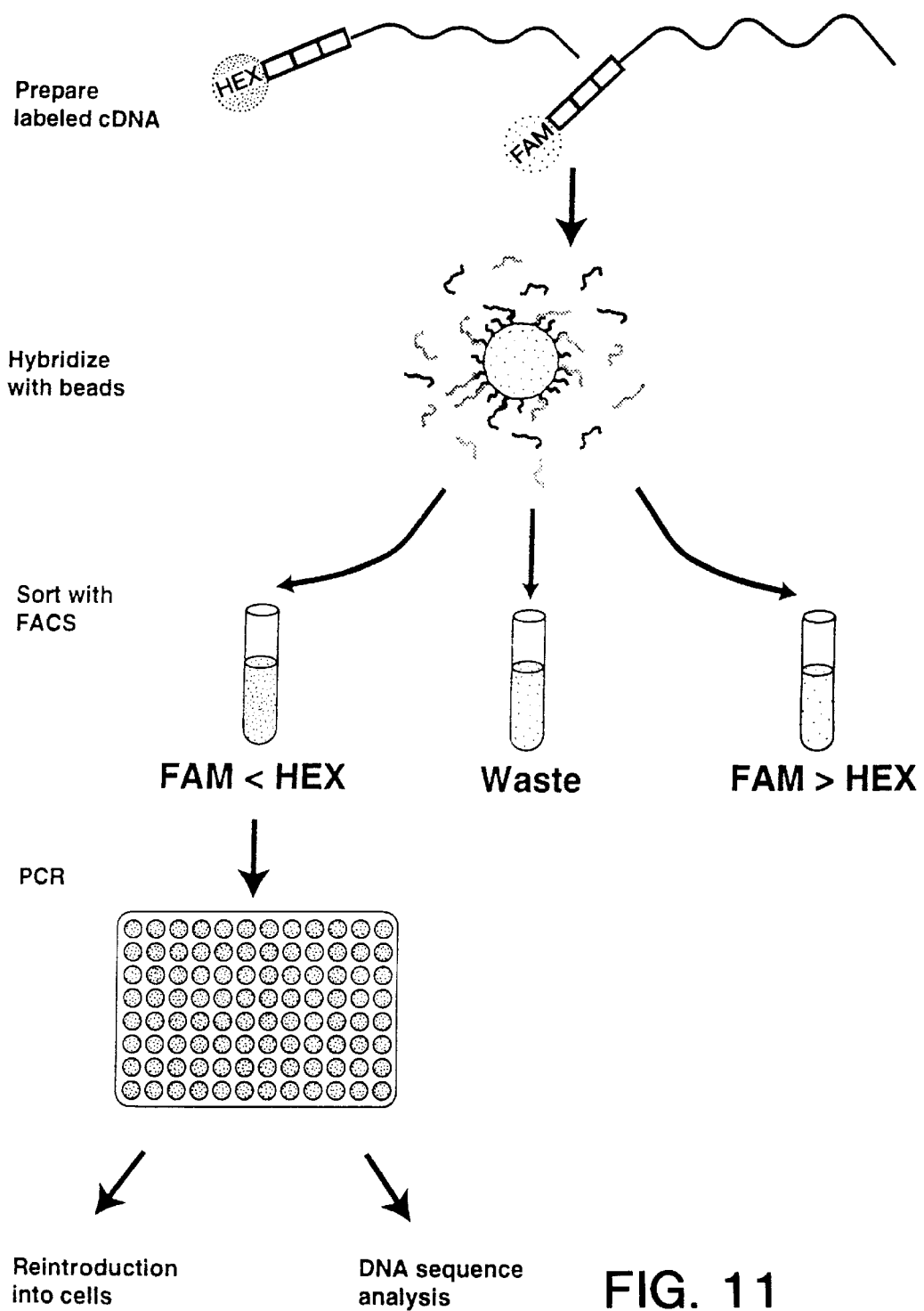
FIG. 11 depicts the enrichment and recovery of cDNAs prepared from two different sources, as described in Example 12, infra.

The following example depicts enrichment and recovery of nucleic acids. cDNAs prepared from two different sources are labeled with fluorophores (e.g., HEX in one case and FAM in another). The labeling can be accomplished in many ways known in the art. For example, the fluorophore can be attached at the 5' end of a primer used to reverse transcribe MRNA, or alternatively, to amplify from cDNA template suitable for PCR. The fluorophore can also be incorporated during synthesis by DNA polymerases as described in Schena et al., supra. cDNAs from two samples are mixed together and hybridized with the beads. Bound cDNA is monitored by fluorescence signal at or near the two emission maxima as the beads pass through the FACS excitation/detection apparatus. The labeled cDNA is mixed with cognate beads so that, for example, one million beads are placed in hybridization buffer (e.g., 5×SSPE, 0.1% Triton) with target cDNA at a final concentration of 10 $\mu$g/ml. The reaction is allowed to proceed (with mixing) for 10 hours at 30° C., at which time the beads are washed three times in 1×SSPE at room temperature. The beads are then diluted into 1 ml PBS plus 0.05% Triton and run through a FACS machine exciting the dyes at 488 nm with an argon laser and measuring fluorescence intensity at two separate wavelengths (530 nm and 585 nm). Initially, the FACS is "tuned" with beads that are labeled exclusively with FAM or with HEX, so that a scaling factor can be applied to the intensity measurements; the scaling factor is simply the ratio of the mean FAM and HEX signals at the two emission wavelengths. This factor provides a correction for differences in labeling efficiency, excitation and emission strengths, etc. The scaling factor can be applied to the real bead fluorescence ratio measurements. Most beads should thus have scaled ratios near one, while a few should deviate. Those that deviate can be collected by sorting, and used individually to provide templates for PCR amplification using primers derived from the two ends of the cDNA. Amplified material can then be reintroduced into cells for another round of enrichment, or can be sequenced, either directly or after cloning first in *E. coli*. See, FIG. 11.

M. Example 13
Post-Passage Library Comparison

The following exemplifies post-passage library comparison.

Figure 12:
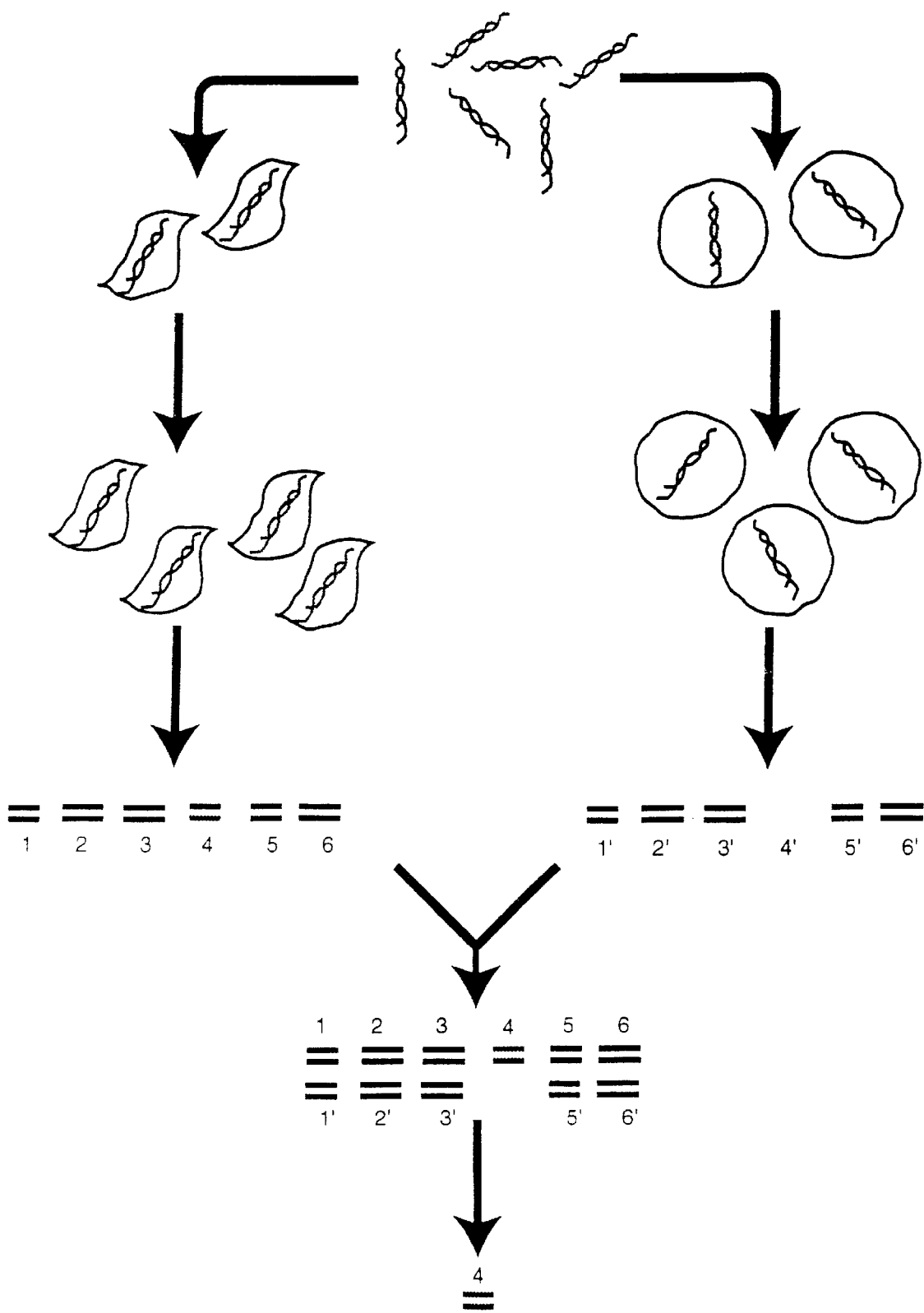
FIG. 12 depicts the concept of post-passage library comparison, as described in Example 13, infra.

A cDNA library, represented in FIG. 12 as double helices, is introduced separately into two cell types. The library can be introduced into cells in a variety of ways including transfection, electroporation, or viral infection. Methods for gene transfer are known in the art. Stable transformants that carry specific library sequences can be isolated using selectable markers carried on the expression vectors used in the gene transfer experiments. Alternatively, the library sequences can be propagated and expressed transiently. After either isolation of stable transformants or establishment of transient cultures, the library sequences can be re-isolated from each cell population using, e.g., PCR to amplify the resident library sequences. PCR primers depend on the details of the library but can be chosen typically so that standard PCR conditions apply. The sequences from the two independently passaged libraries can be labeled and compared by hybridization to beads followed by FACS analysis as in Example 10, infra. Beads that carry sequences from the initial library that have differentially propagated in the two cell populations are visualized by deviations from unity of fluorescence intensity ratios of the labels on sequences harvested from each cell population. These beads of interest can be isolated, their attached library sequences can be eluted and subjected to PCR for analysis.

N. Example 14
Normalization Of cDNA Libraries

Figure 13:
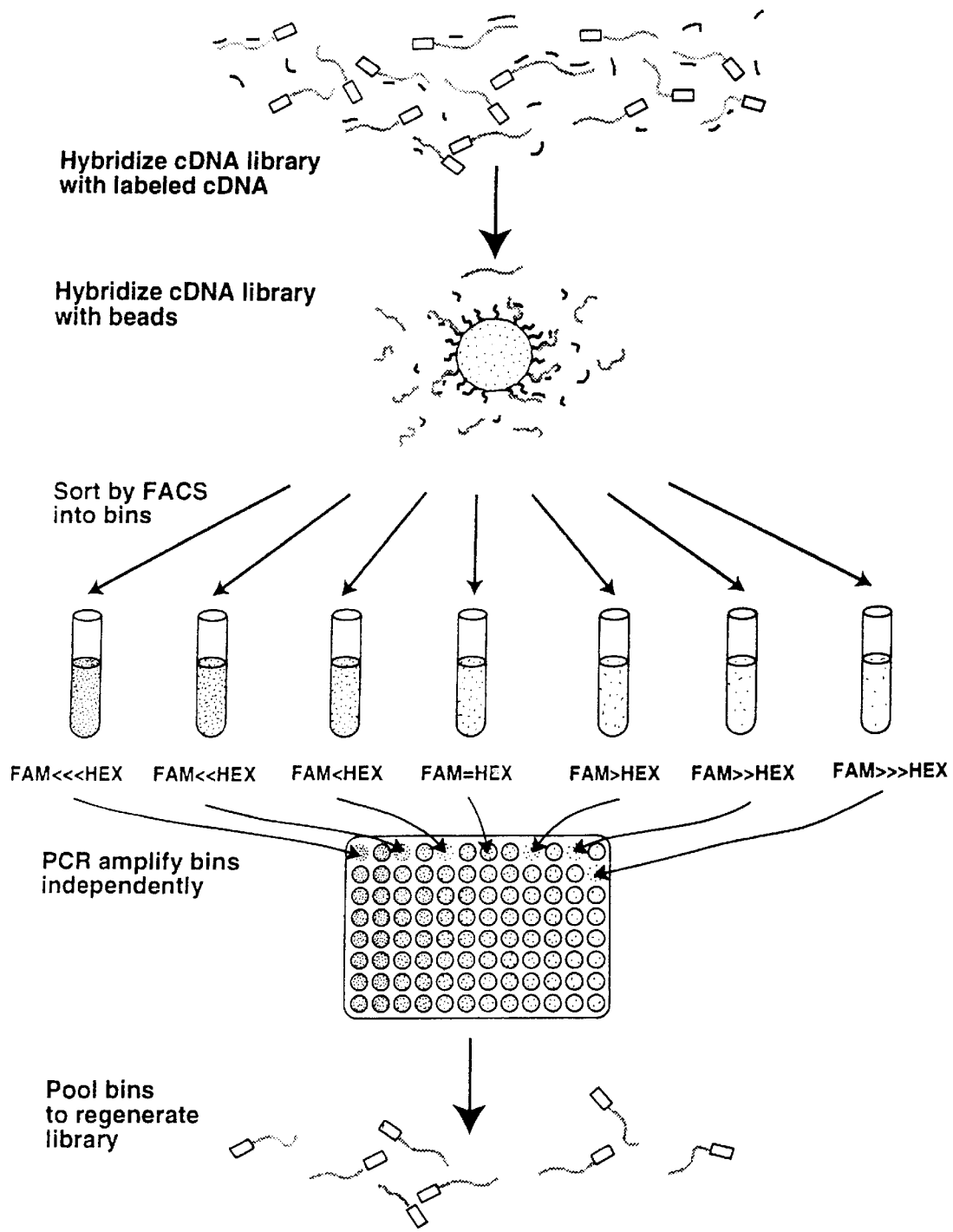
FIG. 13 depicts normalization of cDNA libraries by hybridization to beads using, e.g., the 24-mer identifier tags, grouping of clones according to relative amounts and subsequent adjustment of amounts by, e.g., PCR, to form the final normalized pool of cDNAs, as described in Example 14, infra.

The following example illustrates the normalization of a cDNA library.

cDNA libraries are normalized by hybridization to beads using, e.g., the 24-mer oligonucleotides. The bound cDNA is hybridized in a second step with labeled cDNA from a particular cell type. Small but detectable amounts of 24-mer complement oligonucleotides (labeled with a fluorophore distinct from the cDNA fluorophore) are included in the hybridization to serve as a normalizing signal. (The order of hybridization steps may be varied). The beads are sorted using the FACS into bins that reflect the ratios of the two signals. These bins are amplified independently and remixed in equal amounts with one another to form the final normalized pool of cDNAs. See, FIG. 13.

Alternatively, random oligonucleotides of random or pseudo-random sequence (e.g., random 15-mers) on beads can be used to normalize a library. In this case a labeled cDNA is hybridized to the beads via the 15-mers and sorted based solely on its signal alone.

O. Example 15
Quantitative Comparison Of mRNA Levels

Figure 14:
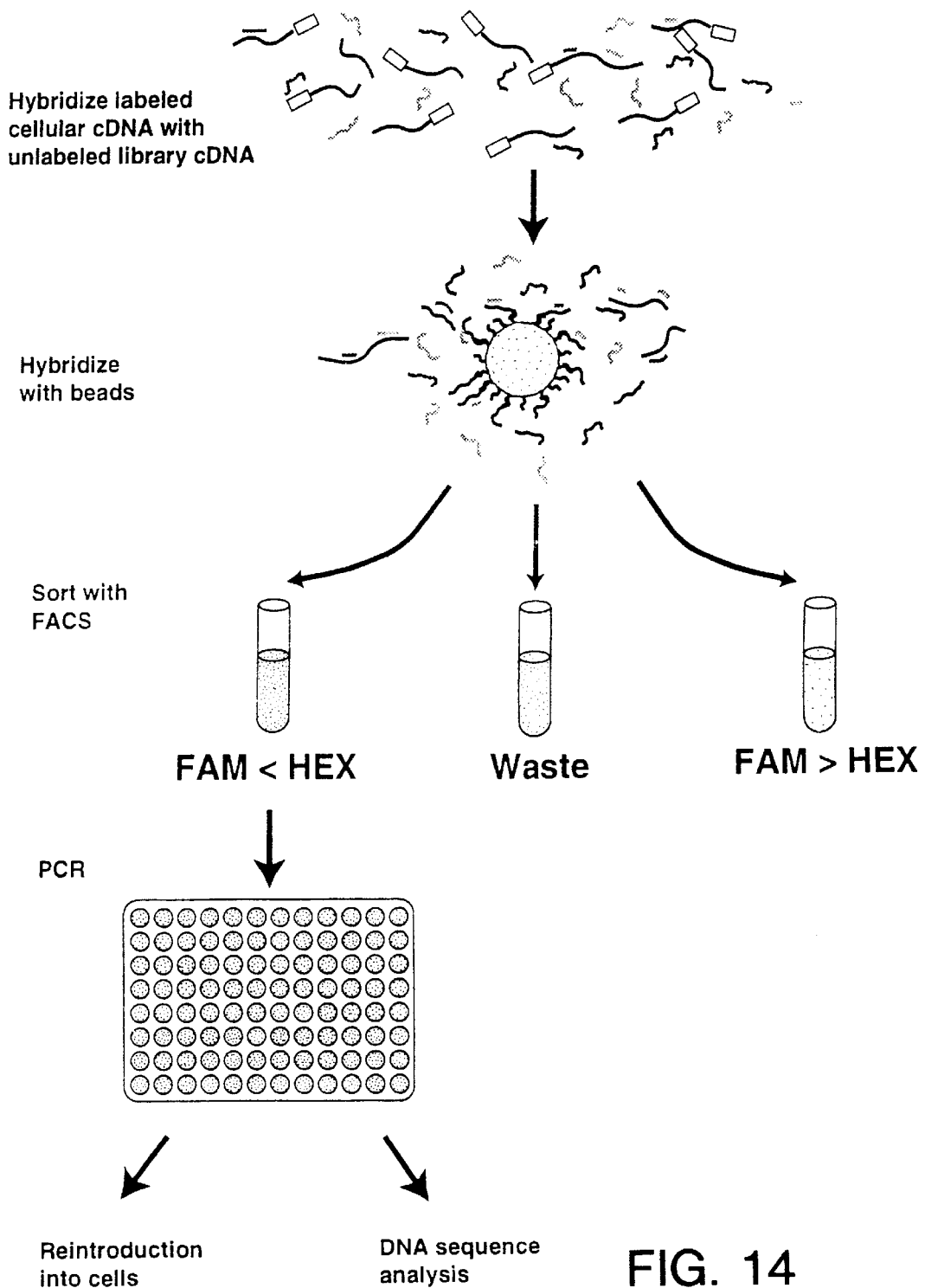
FIG. 14 depicts the quantitative comparison of MRNA levels in a sandwich assay, as described in Example 15, infra.

The following example illustrates the quantitative comparison of mRNA levels.

cDNA libraries that contain the 24-mer identifier tags are hybridized in solution to labeled cDNA produced from two different sources of MRNA, one labeled with, e.g., FAM, one with, e.g., HEX. This mixture is subsequently hybridized to beads that contain 24-mer complements. (The order of these two hybridization steps may be inverted.) The beads are then sorted based on the FAM/HEX fluorescence ratios. The relevant populations of beads are isolated, cDNAs containing the tags are eluted and used as templates for PCR. The amplified cDNAs are sequenced, with or without cloning, or passed through cells. See, FIG. 14.

P. Example 16
Kinetic Genetics

The following example illustrates the use of the present invention for kinetic genetics.

Figure 15A:
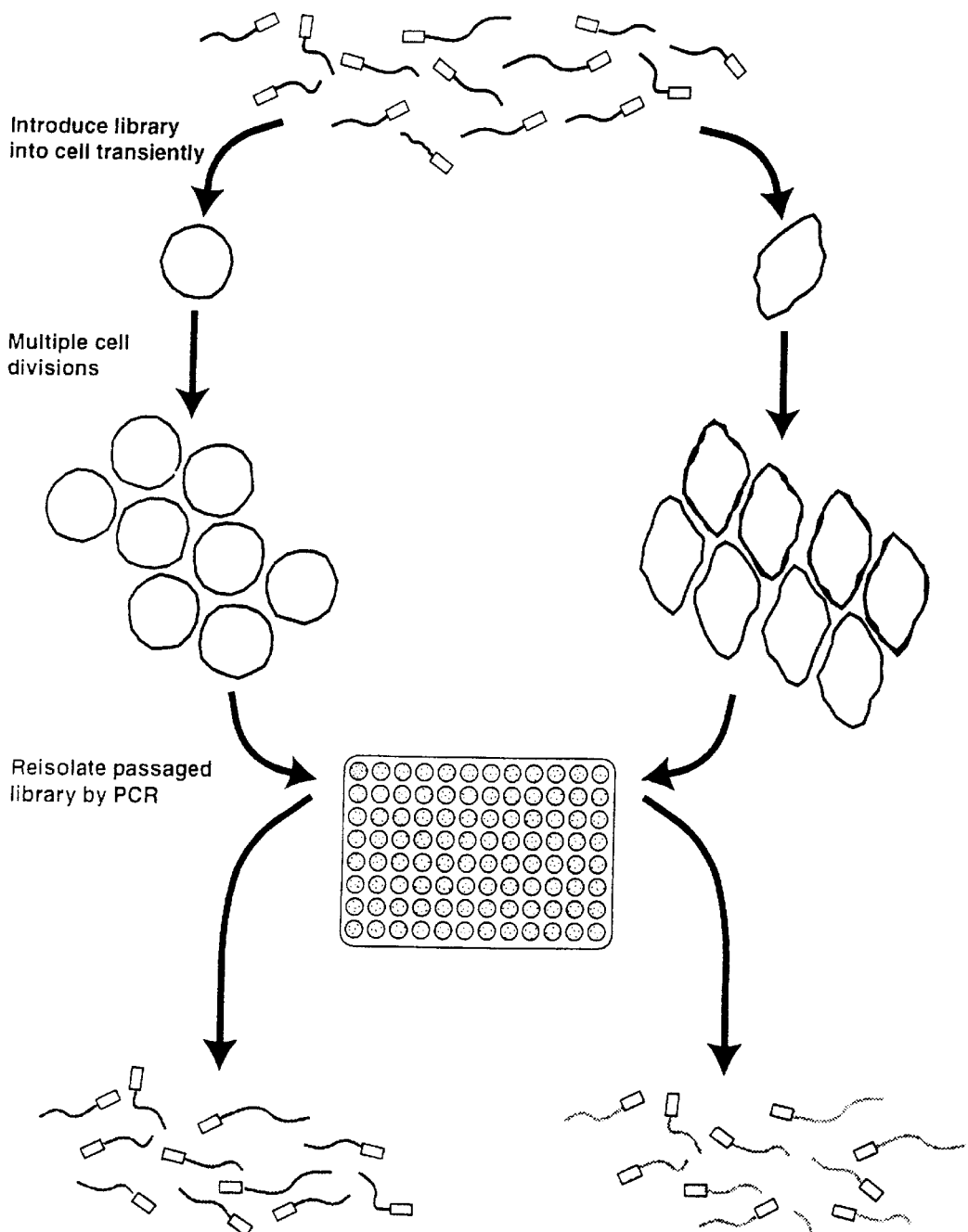
FIGS. 15A and 15B depict kinetic genetics involving the passage of, e.g., a cDNA library through two different cell types, as described in Example 16, infra.
Figure 15B:
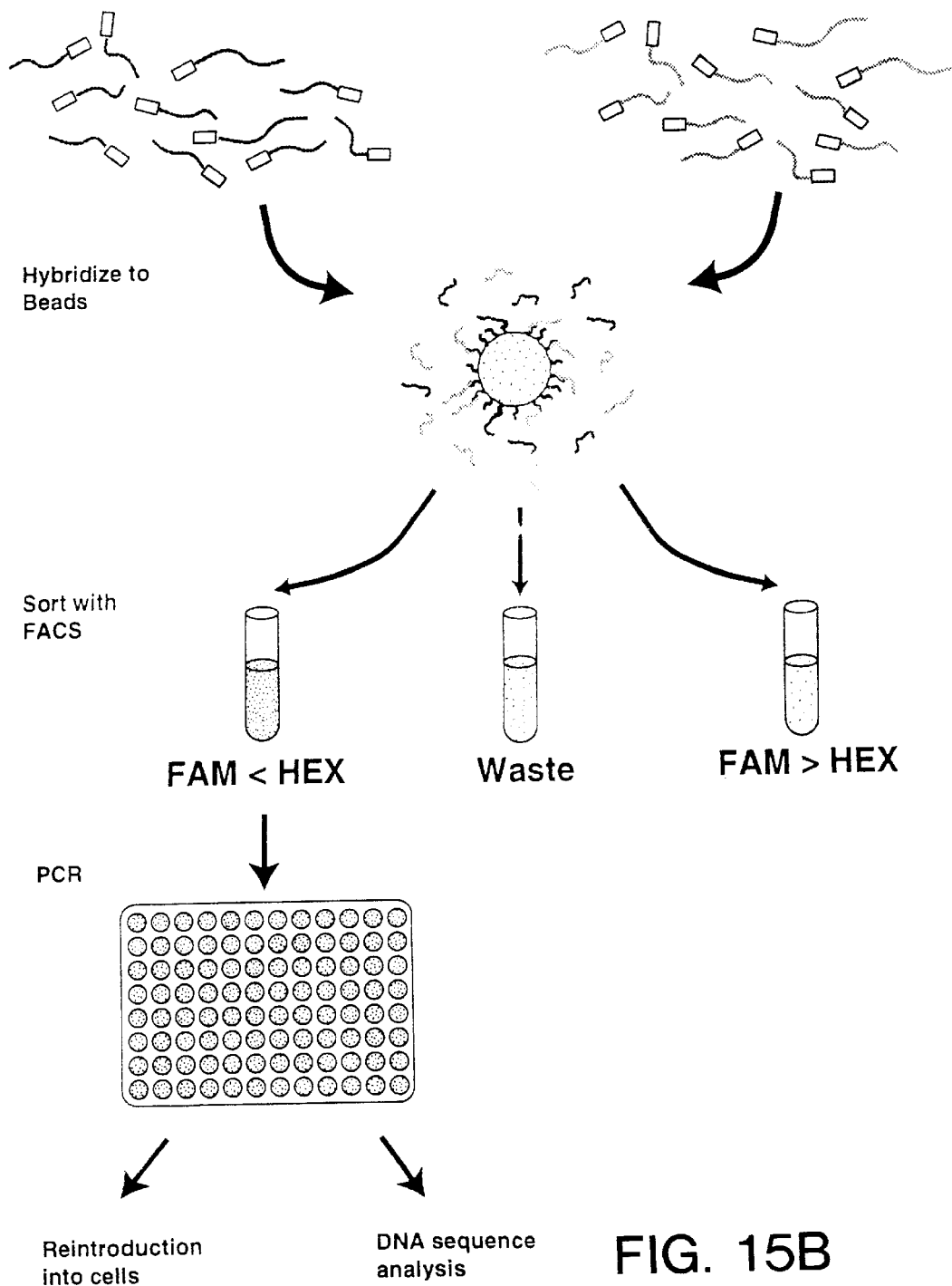

The procedure involves passage of an, e.g., cDNA library through two different cell types, in FIGS. 15A and 15B represented by circles or oblong trapezoids. The DNA is introduced using transient expression procedures that are known in the art such as electroporation, lipofection, viral infection, DEAE dextran, or calcium phosphate precipitation. The cells are allowed to undergo several rounds of cell division, typically between 5 and 20 divisions. Because most transferred mammalian sequences can replicate in host mammalian cells extrachromosomally (or within a chromosomal insertion site), proliferation of the cells is expected to result in multiplication of the transferred sequences. However, since the transferred sequences typically lack a centromere or other sequence that can ensure proper segregation, continued propagation of the cells results in gradual loss of transferred DNA. However, over relatively short numbers of cell divisions, it is likely that sequences that either confer a growth advantage to the host cell, or are neutral in their effect on growth, will increase in abundance as the cells divide. In contrast, sequences that do not replicate or have deleterious effects on cell growth will be preferentially lost. For example, ten cell divisions should result in an increase of $(2)^{10}$ (or roughly one thousand) in the mass of a properly replicating and segregating sequence. If, however, sequence segregation is random during division, half the time one daughter cell does not inherit a sequence (assuming two initial copies per parental cell). This may result in decreased amplification to, e.g., $(1.5)^{10}$ (or roughly sixty). However, these transferred sequences are able to reproduce and can gain a selective advantage over any transferred sequence that causes cell death or inhibits cell growth. If a particular sequence causes cell death in one cell type and has a neutral effect in another, a post-passage comparison of the abundance of that sequence in the two passaged libraries may reveal a significant difference between the libraries.

A potential problem with using transient expression in mammalian cells is the possibility of multiple transferred sequences per cell; i.e., a single cell harbors more than one transferred sequence and thus the selection may apply to "bystander" sequences as well as the sequence of interest. This problem can be circumvented by either multiple rounds of passage (passage, re-isolation of the library, and reintroduction into cells) or methods such as viral infection which limit the number of transferred sequences per cell.

In summary, transient expression has the considerable advantage of speed, ease, and flexibility (since most cells can be transfected transiently), but the disadvantage that the enrichment levels may not be as high as with stably expressing cells. Imperfect replication/segregation will cause increases in neutral sequences that is subgeometric. However, since the "signal" takes the form of relative abundance differences between sequences present in two independently passaged libraries, and since multiple enrichment cycles (see, infra) can be performed, the method provides a rapid, general mechanism for establishing the role of specific sequences on cell growth. For example, if two different sequences from a genetic library, A and B, are propagated in two different cell types for ten (10) generations in which A is neutral but B causes growth arrest in one of the cell types, the following considerations apply: after 10 generations A will have increased, e.g., 60-fold in both cell types so that the ratio of A abundance in both post-passaged libraries is one. However, B increases 60-fold in one cell type but not at all in the other; thus, its ratio is 60. A single round of passaging, therefore results in, e.g., a 60-fold change in the abundance ratio of B in the two passaged libraries. The invention described herein provides the means to detect and isolate sequences that behave in this fashion.

To increase the likelihood that DNA sequences may have effects on cell growth, genetic libraries are constructed in expression vectors suitable for introduction into the host cells and designed to facilitate transcription and translation of the DNA insert sequences from the library. For example, in mammalian cells vectors that contain cytomegalovirus enhancer sequences are useful as are numerous others. In yeast, sequences that contain the GALA enhancer and/or promoter are useful for this purpose. The genetic library used in these post-passage experiments may consist of full-length cDNA clones, cDNA fragments, or genomic DNA fragments. The library may also consist of random or semi-random insert sequences, preferably fused to or inserted into sequences from another relatively stable protein. Such sequences have been termed "perturbagens". See, U.S. patent application Ser. No. 08/699,266, filed Aug. 19, 1996, incorporated hereby by reference in its entirety.

The library sequences, once introduced into and propagated in a particular pair of cell types, may be isolated from each cell type by several methods including PCR (using primer sites that flank the insert), or by transformation of bulk DNA into suitable host cells such as *E.coli*, and recovery of clones that contained selectable markers present on the expression vector such as ampicillin resistance genes.

The library sequences, once recovered, can be amplified and labeled with, e.g., fluorophores such as HEX and FAM (HEX for one sample, FAM for the other). These labeled post-passage library inserts can be hybridized to beads that contain complements of identifier tags that are attached to the library inserts during the original construction of the library. FACS analysis as described infra can then detect beads that have skewed HEX/FAM intensity ratios, and hence sequences that are candidates for inducing selective cell growth, arrest, or death in one cell type and not the other.

All references cited within the body of the instant specification are hereby incorporated by reference in their entirety.

What is claimed is:

1. A method of normalizing a genetic library, comprising the steps of:
    (a) attaching unique oligonucleotide identifier tags to cDNA inserts derived from a genetic library;
    (b) hybridizing the cDNA inserts of step (a) with cDNA derived from a source of interest under conditions that promote the formation of perfectly matched duplexes, wherein the cDNA is labeled with a first label;

(c) contacting the mixture of step (b) with solid supports having attached thereto the complements of the oligonucleotide identifier tags under conditions that promote the formation of perfectly matched duplexes between the oligonucleotide identifier tags and their respective complements in the presence of free oligonucleotide identifier tags labeled with a second label and corresponding in sequence to the oligonucleotide identifier taos of step (a);

(d) sorting solid supports according to the relative amount of said first label and said second label, wherein said relative amount of said first and second label correlates with the abundance of a cDNA, or mRNA sequence; and (e) amplifying cDNA inserts present at lower abundance in order to match the abundance of all cDNA sequences such that they are represented at substantially similar levels in the library.

2. The method of claim 1, wherein said first and said second label are distinguishable fluorescent labels.

3. The method of claim 2, wherein said fluorescent labels are individually selected from the group consisting of 6-FAM, HEX, TET, TAMRA, ROX, JOE, 5-FAM, phycoerythrin and R110.

4. The method of claim 1, wherein the oligonucleotide identifier tag has a length from about 16 to about 32 nucleotides.

5. The method of claim 4, wherein the oligonucleotide identifier tag is a 24-mer.

6. A method for comparing relative amounts of specific nucleic acid molecules in at least two samples wherein the relative abundance of one or more of said molecules changes during propagation in two host cell populations, comprising the steps of:

(a) introducing nucleic acid samples from a single source individually into different cell populations;

(b) propagating the different cell populations;

(c) re-isolating the nucleic acid samples from the propagated cell populations; and (d) subjecting the re-isolated nucleic acid samples to quantitative comparison of the relative amounts of at least one specific nucleic acid molecule.

7. The method of claim 6, further comprising an enrichment step (e), in which the samples from step (c) are subjected to one or more cycles of steps (a) through (c).

8. The method of claim 6, wherein the single nucleic acid source is a genetic library.

9. The method of claim 8, wherein the library comprises inserts selected from the group consisting of genomic DNA, cDNA, and random sequence DNA.

10. The method of claim 8, wherein the genetic library comprises a plurality of inserts, the inserts comprising one or more sequences which, upon expression in a living host cell, are capable of differentially altering the phenotype of the host cell.

11. The method of claim 10, wherein expression of the sequences alters host cell gene expression.

12. A method for identifying specific nucleic acid sequences in a genetic library whose relative abundance changes after propagation in two different cell populations, the method comprising the steps of claim 6 and further comprising the step of:

(e) determining the identity of at least one nucleic acid molecule whose relative abundance differs after propagation in one cell population relative to another cell population.

13. The method of claim 6 or 12, wherein step (d) further comprises:

(d1) differentially labeling nucleic acid samples derived from each library re-isolated from the cell populations to generate a first and a second labeled nucleic acid sample;

(d2) generating a target pool comprising said first and second nucleic acid samples;

(d3) contacting said target pool with a plurality of solid supports each having attached thereto multiple capture oligonucleotides of a unique sequence under conditions which promote the formation of perfectly matched duplexes between said capture oligonucleotides and nucleic acid molecule complements within said target pool; and (d4) sorting the solid supports according to the relative amount of said first label and said second label.

14. The method of claim 13, wherein the solid supports have attached thereto oligonucleotides complementary to nucleic acid molecules representing particular transcripts of interest.

15. The method of claim 13, wherein the unique capture oligonucleotides attached to the solid supports have a length of from about 10 to about 50 nucleotides.

16. The method of claim 13, wherein the unique capture oligonucleotides attached to the solid supports have a length of from about 50 to about 5,000 nucleotides.

17. The method of claim 13, wherein the unique capture oligonucleotides attached to the solid supports comprise a stretch of from about 10 to about 40 nucleotides of random sequence.

18. The method of claim 13, wherein the unique capture oligonucleotides attached to the solid supports have a length of from about 12 to about 30 nucleotides and comprising a stretch of from about 10 to about 20 nucleotides of random sequence.

19. The method of claim 13, wherein the unique capture oligonucleotides attached to the solid supports comprise a combination of from about 2 to about 6 sequence units in tandem configuration, each unit consisting of from about 7 to about 15 nucleotides.

20. The method of claim 13, wherein the unique capture oligonucleotides attached to the solid supports comprise a stretch of from about 5 to about 25 adenosine residues at the 3' end, and a stretch of from about 8 to about 16 nucleotides of random sequence at the 5' end.

21. The method of claim 13, wherein the target nucleic acid molecules have attached thereto unique oligonucleotide identifier tags, each of said tags comprising a combination of from about 2 to about 6 sequence units in tandem configuration, each unit consisting of from about 7 to about 15 nucleotides.

22. The method of claim 21, wherein the capture oligonucleotides attached to said solid supports comprise complements of said unique identifier tags.

23. The method of claim 13, wherein said first and said second label are distinguishable fluorescent labels.

24. The method of claim 23, wherein said fluorescent labels are individually selected from the group consisting of 6-FAM, UEX, TET, TAMRA, POX, JOE, 5-FAM, phycoerythrin and R110.

25. The method of claim 12, wherein the identity of the nucleic acid molecule is determined directly by DNA sequence analysis of the nucleic acids hybridized to the solid support.

26. The method of claim 12, wherein the identity of the nucleic acid molecule is determined indirectly by DNA sequence analysis of the oligonucleotide or fragment attached to the solid support.

27. The method of claim 6, wherein the cell populations in step (a) differ in phenotype.

28. The method of claim 6, wherein the cell populations in step (a) differ in genotype.

29. The method of claim 6, wherein the cell populations in step (a) comprise cells which differ in cell type, tissue type, physiological state, disease state or developmental stage.

30. The method of claim 6, wherein the cell populations in step (a) comprise cancerous and non-cancerous cells, respectively.

31. The method of claim 6, wherein the cell populations in step (a) comprise cells before and after treatment with an agent, respectively.

32. The method of claim 31, wherein the agent is selected from the group consisting of a naturally occurring growth factor, an immunologic factor, a small molecule compound of interest, a putative therapeutic compound, a therapeutic lead compound, and a growth-arresting substance.

33. The method of claim 8, wherein the library is an expression library and the target nucleic acid molecules are RNA transcripts whose relative abundance represents the relative promoter activity of a specific nucleic acid sequence in the library after propagation in the different cell populations.

34. The method of claim 8, wherein the library comprises genomic DNA or random DNA sequence inserts and the relative abundance of the target nucleic acid molecules represents the relative differences in copy number of a specific nucleic acid sequence in the library after propagation in the different cell populations.

35. The method of claim 1, wherein the unique oligonucleotide identifier tag has a length of from about 14 to about 90 nucleotides.

36. The method of claim 1, wherein the unique oligonucleotide identifier tag comprises a combination of from about 2 to about 6 sequence units in tandem configuration, each unit consisting of from about 7 to about 15 nucleotides.

* * * * *

```
                             SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
           (A) LENGTH: 20 base pairs
           (B) TYPE: nucleic acid
           (C) STRANDEDNESS: unknown
           (D) TOPOLOGY: unknown (xi) SEQUENCE DESCRIPTION: SEQ ID NO:1:

GCTGCATAAA CCGACTACAC                                                   20

(2) INFORMATION FOR SEQ ID NO:2:

(i) SEQUENCE CHARACTERISTICS:
           (A) LENGTH: 20 base pairs
           (B) TYPE: nucleic acid
           (C) STRANDEDNESS: unknown
           (D) TOPOLOGY: unknown (xi) SEQUENCE DESCRIPTION: SEQ ID NO:2:

GCATTATCCG AACCATCCGC                                                   20

(2) INFORMATION FOR SEQ ID NO:3:

(i) SEQUENCE CHARACTERISTICS:
           (A) LENGTH: 20 base pairs
           (B) TYPE: nucleic acid
           (C) STRANDEDNESS: unknown
           (D) TOPOLOGY: unknown (xi) SEQUENCE DESCRIPTION: SEQ ID NO:3:

CCGAGTGTGA TCATCTGGTC                                                   20
```